United States Patent
Schliephake et al.

(10) Patent No.: US 8,263,802 B2
(45) Date of Patent: Sep. 11, 2012

(54) PROCESS FOR REDISSOCIATING MICHAEL ADDUCTS WHICH ARE PRESENT IN A LIQUID F AND HAVE BEEN FORMED IN THE PREPARATION OF ACRYLIC ACID OR ESTERS THEREOF

(75) Inventors: Volker Schliephake, Schifferstadt (DE); Thorsten Friese, Mannheim (DE); Klaus Bott, Ludwigshafen (DE); Michael Blechschmitt, Schifferstadt (DE); Till Blum, Kuantan (MY); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 350 days.

(21) Appl. No.: 12/634,143

(22) Filed: Dec. 9, 2009

(65) Prior Publication Data

US 2010/0152482 A1 Jun. 17, 2010

Related U.S. Application Data

(60) Provisional application No. 61/122,154, filed on Dec. 12, 2008.

(30) Foreign Application Priority Data

Dec. 12, 2008 (DE) .......................... 10 2008 054 587

(51) Int. Cl.
*C07C 265/00* (2006.01)

(52) U.S. Cl. ........ 560/352; 560/205; 560/216; 560/224; 560/260

(58) Field of Classification Search .................. None
See application file for complete search history.

(56) References Cited

U.S. PATENT DOCUMENTS

| | | | | |
|---|---|---|---|---|
| 6,454,541 | B1 * | 9/2002 | Ijiri et al. | 417/53 |
| 6,870,066 | B2 * | 3/2005 | Shibusawa et al. | 560/216 |
| 6,939,991 | B2 * | 9/2005 | Thiel et al. | 562/545 |
| 7,612,230 | B2 * | 11/2009 | Shima et al. | 562/535 |
| 7,910,771 | B2 * | 3/2011 | Dubois et al. | 562/532 |
| 2008/0149319 | A1 | 6/2008 | Lipowsky et al. | |
| 2009/0134357 | A1 * | 5/2009 | Bub et al. | 252/194 |

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

A process for redissociating Michael adducts which are present in a liquid F with a proportion by weight of $\geq 10\%$ by weight and have been formed in the preparation of acrylic acid or esters thereof in a redissociating apparatus which comprises a pump P, a separating column K with separating internals and a circulation heat exchanger UW, wherein, for the purpose of supplying the cleavage energy, the pump P sucks in bottoms liquid from the bottom space of the separating column K and, via the circulation heat exchanger UW, continually recycles it into the bottom space above the level of the bottoms liquid, and wherein the pump P is a radial circulation pump with an open impeller.

15 Claims, 11 Drawing Sheets

PROCESS FOR REDISSOCIATING MICHAEL ADDUCTS WHICH ARE PRESENT IN A LIQUID F AND HAVE BEEN FORMED IN THE PREPARATION OF ACRYLIC ACID OR ESTERS THEREOF

CROSS REFERENCE TO RELATED APPLICATIONS

This application claims priority to U.S. Provisional Patent Application No. 61/122,154, filed Dec. 12, 2008, and to German Application No. 102008054587.2, filed Dec. 12, 2008, the enclosures of which are incorporated herein in their entireties, by reference.

Figure 8:
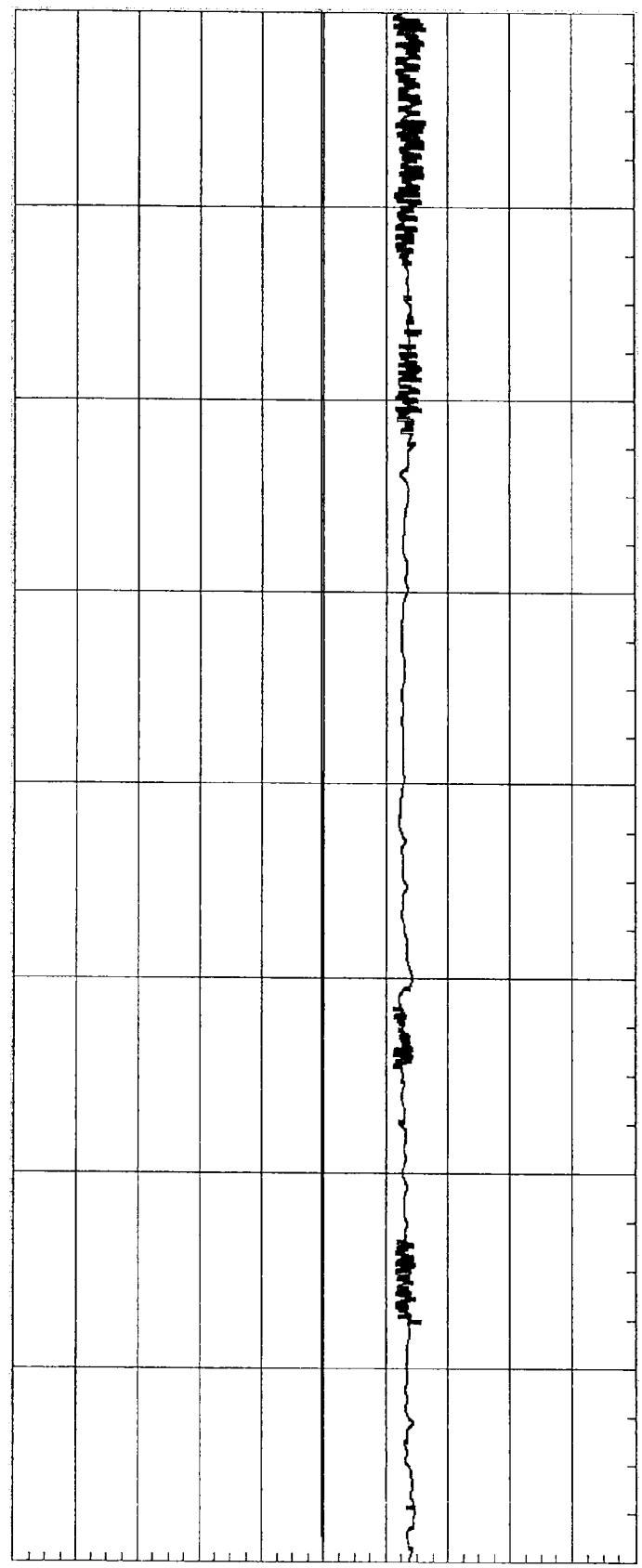
FIG. 8 shows, for the redissociation Example over a section of 7 operating days (point of intersection of the abscissa with the ordinate=start of the 7-day period; right-hand end of the abscissa=end of the 7-day period) the profile of the flow rate circulated by a centrifugal pump with a semiopen impeller.
Figure 9:
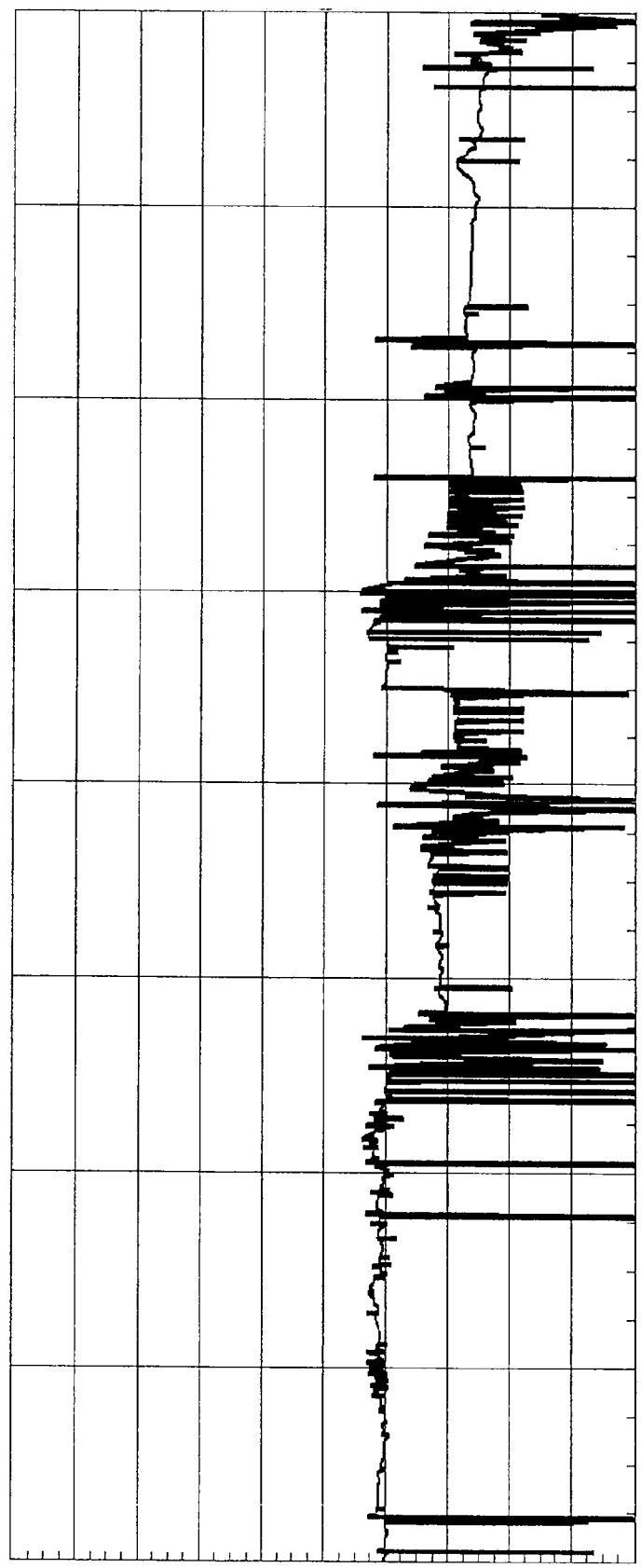
FIG. 9 shows for the same redissociation process as FIG. 8 and also over a section of 7 operating days (point of intersection of the abscissa with the ordinate=start of the 7-day period; right-hand end of the abscissa=end of the 7-day period) the profile of the corresponding flow rate now circulated as Comparison Example by a corresponding radial centrifugal pump with a closed impeller.

The ordinates of FIGS. 8 and 9 have identical scales.

Figure 10:
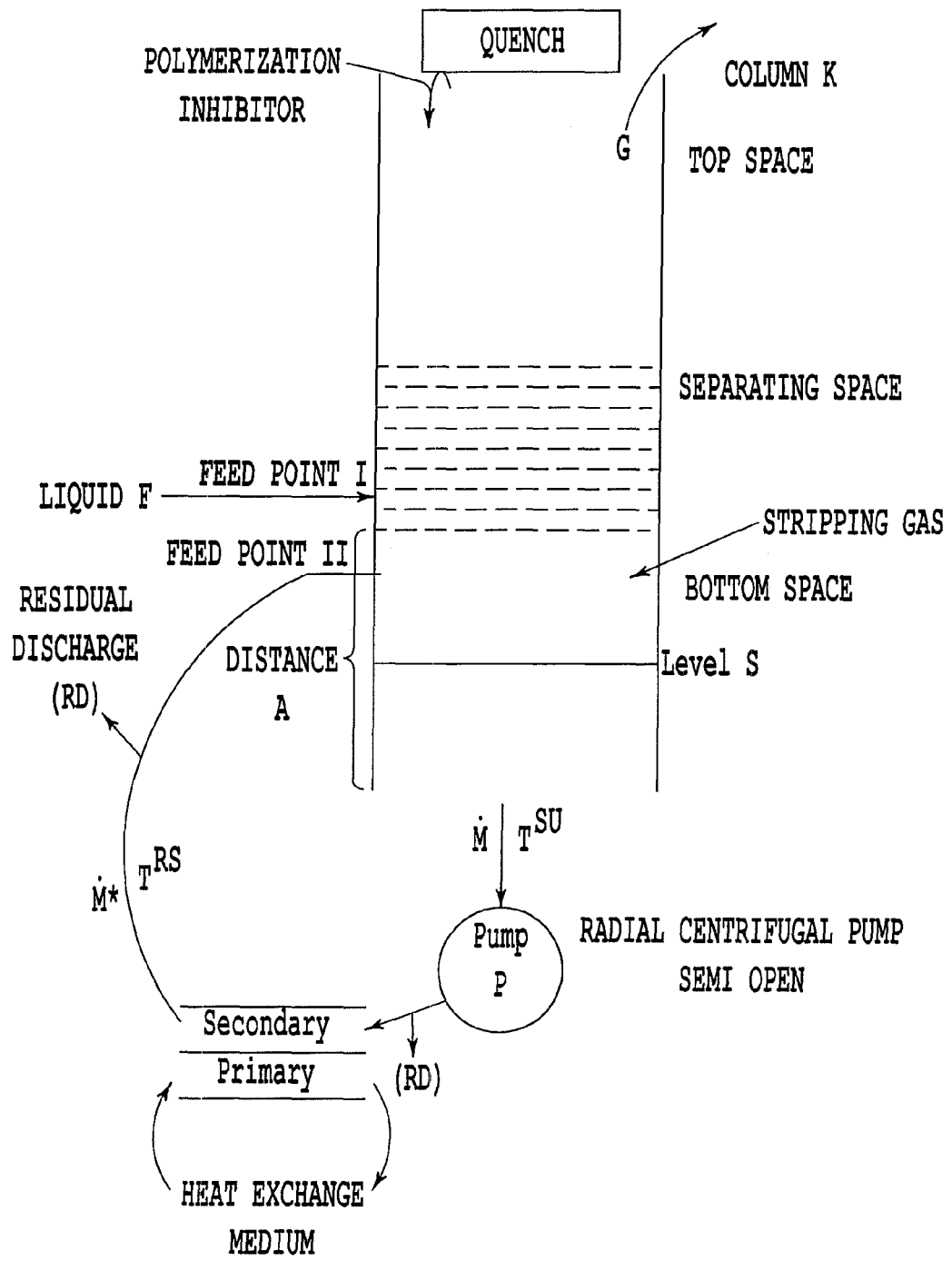

FIG. 10 is a schematic diagram of the process flow of the process according to claim 15.

The present invention relates to a process for redissociating Michael adducts which are present in a liquid F with a proportion by weight, based on the weight of the liquid F, of ≧10% by weight and have been formed in the preparation of acrylic acid or esters thereof in a redissociating apparatus which comprises at least one pump P, a separating column K which consists, from the bottom upward, of a bottom space, a separating space which adjoins the bottom space and comprises separating internals, and a top space which adjoins the separating space, and in which the pressure in the gas phase decreases from the bottom upward, and an indirect circulation heat exchanger UW which has at least one secondary space and at least one primary space separated from the at least one secondary space by a material dividing wall D, in which the liquid F is conducted continuously into the separating column K with the feed temperature $T^Z$ at a feed point I which is above the lowermost separating internal in the separating column K, and, at the lowest point in the bottom space of the separating column K, the pump P is used to continuously withdraw a mass flow $\dot{M}$ of the liquid which effluxes into the bottom space through the separating internals and comprises Michael adducts with a temperature $T^{SU}$ so as to establish, in the bottom space, as the bottoms liquid, a level S of the liquid effluxing into it which is less than half the distance A, measured from the lowest point in the separating column K to the underside of the lowermost separating internal in the separating column K, while a gas pressure GD exists in the remaining space of the bottom space above this liquid level, and at least one substream I of the mass flow $\dot{M}$ is conducted through the at least one secondary space of the indirect circulation heat exchanger UW while being heated, by indirect heat exchange with a fluid heat carrier conducted simultaneously through the at least one primary space of the circulation heat exchanger UW, to a redissociation temperature $T^{RS}$ above the temperature $T^{SU}$, and at least one substream II from the mass flow $\dot{M}^*$ conducted out of the at least one secondary space of the circulation heat exchanger UW with the temperature $T^{RS}$ is recycled into the bottom space of the separating column K at a feed point II which is below the lowermost separating internal of the separating column K and above the level S of the bottoms liquid, in such a way that the at least one substream II in the bottom space of the separating column K is not directed toward the bottoms liquid, and a substream at least of one of the two streams $\dot{M}$, $\dot{M}^*$ is discharged as a residual stream, with the proviso that the redissociation temperature $T^{RS}$ is such that, firstly, as it flows through the at least one secondary space of the circulation heat exchanger UW, at least a portion of the Michael adducts present in the at least one substream I is redissociated to form the corresponding redissociation products, and, secondly, the at least one substream II recycled into the separating column K boils at the gas pressure GD existing in the bottom space at the feed point II, and the gas phase which forms in the course of boiling and comprises at least a portion of the redissociation products, following the gas pressure which decreases in the separating column K toward the top space of the separating column K, flows as a gas stream G comprising redissociation products into the top space of the separating column K and the gas stream G is partly condensed by direct and/or indirect cooling still in the top space of the separating column K and/or conducted out of the top space of the separating column K, the condensate formed is recycled at least partly as reflux liquid into the separating column K and the gas stream which remains in the partial condensation is discharged.

Acrylic acid is an important intermediate which finds use, for example, in the preparation of polymer dispersions (including in the form of esters thereof with alcohols) and water-superabsorbent polymers.

Acrylic acid is obtainable, among other methods, by heterogeneously catalyzed gas phase partial oxidation of $C_3$ precursor compounds of acrylic acid (this term shall encompass especially those chemical compounds which are obtainable in a formal sense through reduction of acrylic acid; known $C_3$ precursors of acrylic acid are, for example, propane, propene, acrolein, propionaldehyde and propionic acid; however, the term shall also comprise precursor compounds of the aforementioned compounds, for example, glycerol (proceeding from glycerol, acrylic acid can be obtained, for example, by heterogeneously catalyzed oxidative dehydration in the gas phase; cf., for example, EP-A 1 710 227, WO 06/114506 and WO 06/092272)) with molecular oxygen over solid state catalysts at elevated temperature (e.g. German Application 102007055086.5 and DE-A 10 2006 062 258).

Owing to numerous parallel and further reactions which proceed in the course of the catalytic gas phase partial oxidation, and owing to the inert diluent gases which have to be used in the partial oxidation, the catalytic gas phase oxidation does not afford pure acrylic acid, but a reaction gas mixture (a product gas mixture) which comprises essentially acrylic acid, the inert diluent gases and by-products, from which the acrylic acid has to be removed.

Typically, the acrylic acid is removed from the reaction gas mixture, among other methods, by first converting the acrylic acid from the gas phase to the condensed (liquid) phase by employing absorptive and/or condensative measures. The further removal of the acrylic acid from the liquid phase thus obtained is subsequently undertaken typically by means of extractive, distillative, desorptive, crystallizative and/or thermal separation processes.

Alternatively, acrylic acid can also be prepared by homogeneously catalyzed processes proceeding from for example, acetylene (e.g. Reppe process) or ethylene (oxycarbonylation). For the removal of the acrylic acid from the resulting reaction mixtures, the above applies in a corresponding manner.

A disadvantage of acrylic acid and the aforementioned separating processes is that acrylic acid present in the liquid phase tends to form undesired by-products.

Such an undesired side reaction is free-radical polymerization with itself to form acrylic acid polymer or oligomer. A disadvantage of this side reaction is that it is essentially irreversible, and monomeric acrylic acid converted to free-radical acrylic acid polymer is therefore lost to the acrylic acid preparation process and reduces the acrylic acid yield of the preparation process. However, an advantage of the undesired free-radical polymerization of acrylic acid is that it can at least be reduced by adding polymerization inhibitors.

The latter is not the case for the second undesired side reaction of acrylic acid in liquid phase. This side reaction is the so-called Michael addition of an acrylic acid molecule onto another acrylic acid molecule, to form a dimeric Michael adduct (Michael diacrylic acid), which can continue through further Michael addition of acrylic acid molecules ("monomeric acrylic acid") onto Michael adducts which have already formed to form Michael acrylic acid oligomers.

Such Michael adducts can be characterized by the general formula I,

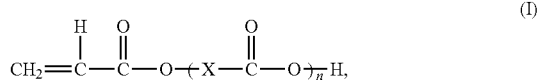

in which n is an integer $\geq 1$, and —X⁻ is —CH$_2$—CH$_2$— or

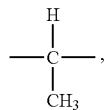

where, in the case that n$\geq$2, all X may be identical or else different. n is unlimited in principle, but varies primarily within the range from 1 to 15, or from 1 to 10. In the presence of protic acids, for example water, and at elevated temperature, the Michael addition proceeds at an accelerated rate.

Esters of acrylic acid are prepared on the industrial scale predominantly by direct reaction of acrylic acid with the corresponding alcohols in liquid phase.

However, in this case too, generally liquid product mixtures are initially obtained, from which the acrylic esters have to be removed. These product mixtures generally comprise free-radical polymers of the starting acrylic acid and/or of the product esters as undesired by-products. However, they also comprise Michael adducts of the general formula (I), which form in an unavoidable manner from the starting acrylic acid in the liquid reaction phase.

Owing to the presence of free alcohol in the liquid esterification reaction mixture, the Michael adducts of the general formula (I), as a result of reaction (substitution or esterification) with such free alcohol R—OH(R=organic radical), may additionally be present in the product mixture of an acrylic acid esterification at least in a form derivatized according to the two following general formulae (II) and (III):

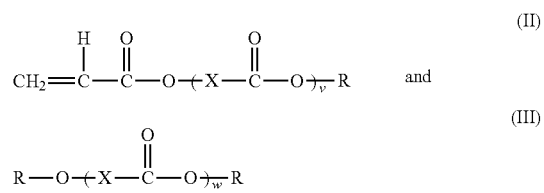

in which X is as defined in the general formula (I), and v and w in turn are each an integer $\geq 1$ (v and w are primarily in the range from 1 to 15, or from 1 to 10).

Compounds of the general formulae (I), (II) and (III) shall therefore be summarized in this document under the term "Michael adducts" (which have been formed in the preparation of acrylic acid or esters thereof). When the prefix "Michael" is absent in this document, the terms "oligomer" and "polymer" mean the compounds which arise through free-radical reaction.

In contrast to the free-radical polymerization of acrylic acid and/or esters thereof, the formation reactions of the Michael adducts are typically reversible formation reactions. For instance, it is known that Michael adducts (I), (II) and (III), for example through the action of heat, at least partly reform the reactants bound in chemical form therein, acrylic acid, alcohol of esterification and esters of acrylic acid with the alcohol of esterification (cf., for example, DE-A 197 01 737, DE-A 23 39 519, EP-A 1 357 105, EP-A 780 360). Since the boiling points of these reactants are generally below the corresponding Michael adducts (from which they have been reformed), the reactants reformed can be removed continuously from the reaction equilibrium by superimposition of an appropriate pressure gradient, thus allowing the back reaction to be completed gradually.

A recovery of the reactants present in chemically bound form in the Michael adducts brought about in this way is desirable in that it allows the target product yield in the preparation of acrylic acid or esters thereof to be increased.

Owing to their comparatively elevated boiling points, the Michael adducts are generally obtained as a constituent of bottoms liquids in the thermal separation of liquid reaction product mixtures in the course of preparation of acrylic acid or esters thereof. Typically, such bottoms liquids comprise, based on their weight, $\geq$10% by weight of Michael adducts.

Furthermore, such liquids comprising Michael adducts, as well as acrylic acid and/or esters thereof, typically also comprise other constituents whose boiling points are different from those of the Michael adducts.

These boiling points may be either below or above those of the Michael adducts. Therefore, when liquids comprising Michael adducts which have been formed in the preparation of acrylic acid or esters thereof are subjected to a process for redissociating the Michael adducts present therein by supplying thermal energy (and optionally in the presence of suitable redissociation catalysts), the resulting cleavage gas comprising at least a portion of the redissociation products is preferably subjected to a countercurrent rectification in order to recover the redissociation products present in the cleavage gas with increased purity (cf., for example, WO 2004/035514, EP-A 780 360 and DE-A 10 2007 004 960).

Typically, a process for redissociating Michael adducts present in a liquid with a proportion by weight, based on the weight of the liquid, of $\geq 10\%$ by weight, which have been formed in the course of preparation of acrylic acid or esters thereof, is performed therefore in a redissociating apparatus as described in the preamble of this document.

The pump P used is normally a radial centrifugal pump with a closed impeller (cf. DE-A 102 28 859). The principle of a centrifugal pump is explained by the example which follows.

If a spoon is used to stir a water-filled glass, the pressure in the center falls and the liquid at the edge of the glass rises as a result of the higher pressure which exists there.

The faster the stirring, the higher the liquid rises. If the glass had a lateral bore or an overflow above the original level, water would flow out there. In the case of a centrifugal pump, the function of the spoon is assumed by a rotating impeller equipped with conveying vanes. The liquid to be conveyed, which enters the pump, is pulled in by the conveying vanes of the rotating impeller, which initially forces it along a circular path. On this path, the fluid accelerated by transfer of momentum flows radially outward, where it flows away through the outlet. Widening of the flow cross section allows the increased speed to be converted proportionally to pressure. When the liquid to be conveyed is conveyed by the impeller essentially parallel to the axis of the impeller drive shaft, reference is made to a centrifugal pump with axial impeller, or else to an axial centrifugal pump.

When the liquid to be conveyed is conveyed by the impeller essentially at right angles to the axis of the impeller drive shaft (radial flow), reference is made to a centrifugal pump with radial impeller, or else to a radial centrifugal pump.

Since, in the case of the radial centrifugal pump, the liquid to be conveyed leaves the impeller radially, i.e. at right angles to the drive shaft, the principle of operation of the radial centrifugal pump, in contrast to the axial centrifugal pump, requires deflection of the conveyed stream. This deflection of the flow achieves higher centrifugal forces in the impeller, which lead to higher conveying pressures. When, in the case of a radial impeller, the impeller vanes at both ends (top and bottom) are connected to a plate each (top plate and base plate), reference is made to a closed radial impeller. The closure of the radial impeller increases the hydraulic efficiency of the radial centrifugal pump and stabilizes the impeller in operation. Owing to these advantages, the radial centrifugal pump with a closed radial impeller is the pump usually used to convey liquids.

However, a disadvantage of the use of a radial centrifugal pump in a process according to the preamble of this document has been found to be that it does not ensure stable long-term conveying output. Instead, the conveying output declined in an unsystematic manner from time to time.

It was therefore an object of the present invention to provide an improved redissociation process.

Accordingly, a process is provided for redissociating Michael adducts which are present in a liquid F with a proportion by weight, based on the weight of the liquid F, of $\geq 10\%$ by weight (of at least 10% by weight) and have been formed in the preparation of acrylic acid or esters thereof in a redissociating apparatus which comprises at least one pump P, a separating column K which consists, from the bottom upward, of a bottom space, a separating space which adjoins the bottom space and comprises separating internals, and a top space which adjoins the separating space, and in which the pressure in the gas phase decreases from the bottom upward, and an indirect circulation heat exchanger UW ("cleavage reactor") which has at least one secondary space and at least one primary space separated from the at least one secondary space by a material dividing wall D, in which the liquid F is conducted continuously into the separating column K with the feed temperature $T^Z$ at a feed point I which is above the lowermost separating internal in the separating column K, and, at the lowest point in the bottom space of the separating column K, the pump P is used to continuously withdraw a mass flow $\dot{M}$ of the liquid which effluxes into the bottom space through the separating internals and comprises Michael adducts with a temperature $T^{SU}$ so as to establish, in the bottom space, as the bottoms liquid, a level S of the liquid effluxing into it which is less than half the distance A, measured from the lowest point in the separating column K to the underside of the lowermost separating internal in the separating column K, while a gas pressure GD exists in the remaining space of the bottom space above this liquid level, and at least one substream I of the mass flow $\dot{M}$ is conducted through the at least one secondary space of the indirect circulation heat exchanger UW while being heated, by indirect heat exchange with a fluid heat carrier conducted simultaneously through the at least one primary space of the circulation heat exchanger UW, to a redissociation temperature $T^{RS}$ above the temperature $T^{SU}$, and at least one substream II from the mass flow $\dot{M}^*$ conducted out of the at least one secondary space of the circulation heat exchanger UW with the temperature $T^{RS}$ is recycled into the bottom space of the separating column K at a feed point II which is below the lowermost separating internal of the separating column K and above the level S of the bottoms liquid (the liquid which effluxes into the bottom space of the separating column K), in such a way that the at least one substream II in the bottom space of the separating column K is not directed toward the bottoms liquid, and a substream at least of one of the two streams $\dot{M}$, $\dot{M}^*$ is discharged as a residual stream, with the proviso that the redissociation temperature $T^{RS}$ is such that, firstly, as it flows through the at least one secondary space of the circulation heat exchanger UW, at least a portion of the Michael adducts present in the at least one substream I is redissociated, and, secondly, the at least one substream II recycled into the separating column K boils at the gas pressure GD existing in the bottom space at the feed point II, and the gas phase which forms in the course of boiling and comprises at least a portion of the redissociation products, following the gas pressure which decreases in the separating column K toward the top space of the separating column K, flows as a gas stream G comprising redissociation products into the (to the) top space of the separating column K and the gas stream G is partly condensed by direct and/or indirect cooling still in the top space of the separating column K and/or conducted out of the top space of the separating column K, the condensate formed is recycled at least partly as reflux liquid into the separating column K and the gas stream which remains in the partial condensation is discharged, wherein the pump P is a radial centrifugal pump with a semiopen radial impeller.

A semiopen radial impeller is understood to mean a radial impeller which has only a base plate and no top plate. This means that, in the case of a semiopen impeller, the impeller vanes are joined with a plate only on one side.

Radial centrifugal pumps with closed or semiopen (radial) impeller are described, for example, in Strömungsmaschinen [Flow Machines], 5th edition, Teubner Verlag (2006) and in Pumpen in der Feuerwehr [Pumps in the Fire Service], part I, Einführung in die Hydromechanik [Introduction to Hydromechanics], Wirkungsweise der Kreiselpumpen [Mode of Operation of Centrifugal Pumps], 4th edition 1998, Verlag W. Kohlhammer, Berlin.

As already described, in a radial centrifugal pump with semiopen radial impeller, the rotating impeller (of the conveying element connected to the drive shaft) transfers work in the form of kinetic energy from the impeller to the liquid to be conveyed. The kinetic energy is converted downstream of the impeller, for example in a stator and/or in the spiral housing of the pump, predominantly back to static pressure (pressure energy, law of the conservation of energies). In principle, a semiopen radial impeller is a simple plate (the baseplate) on which vanes are mounted, as shown by way of example in FIG. 1. The vanes give rise to vane channels whose cross section normally increases very significantly from the inside outward owing to the increasing circumference (see dotted line in FIG. 1). These vane channels cause as much liquid to be conveyed away as can flow into the middle of the impeller. In contrast to the semiopen impeller, which is shown by way of example in FIG. 1, the vane channels in the closed radial impeller are covered in a simple manner by a second plate (the top plate), which has an orifice in the middle (see, for example, FIG. 2). The plan view of a semiopen radial vane impeller (impeller) is shown by way of example by FIG. 3. The vane curvature generally runs in the manner of the natural path of a water droplet on a rotating round, smooth baseplate from the point of view of a co-rotating observer, when the droplet is allowed to fall on the middle of the plate. This vane form is referred to as "backward-curved" vane.

Figure 4:
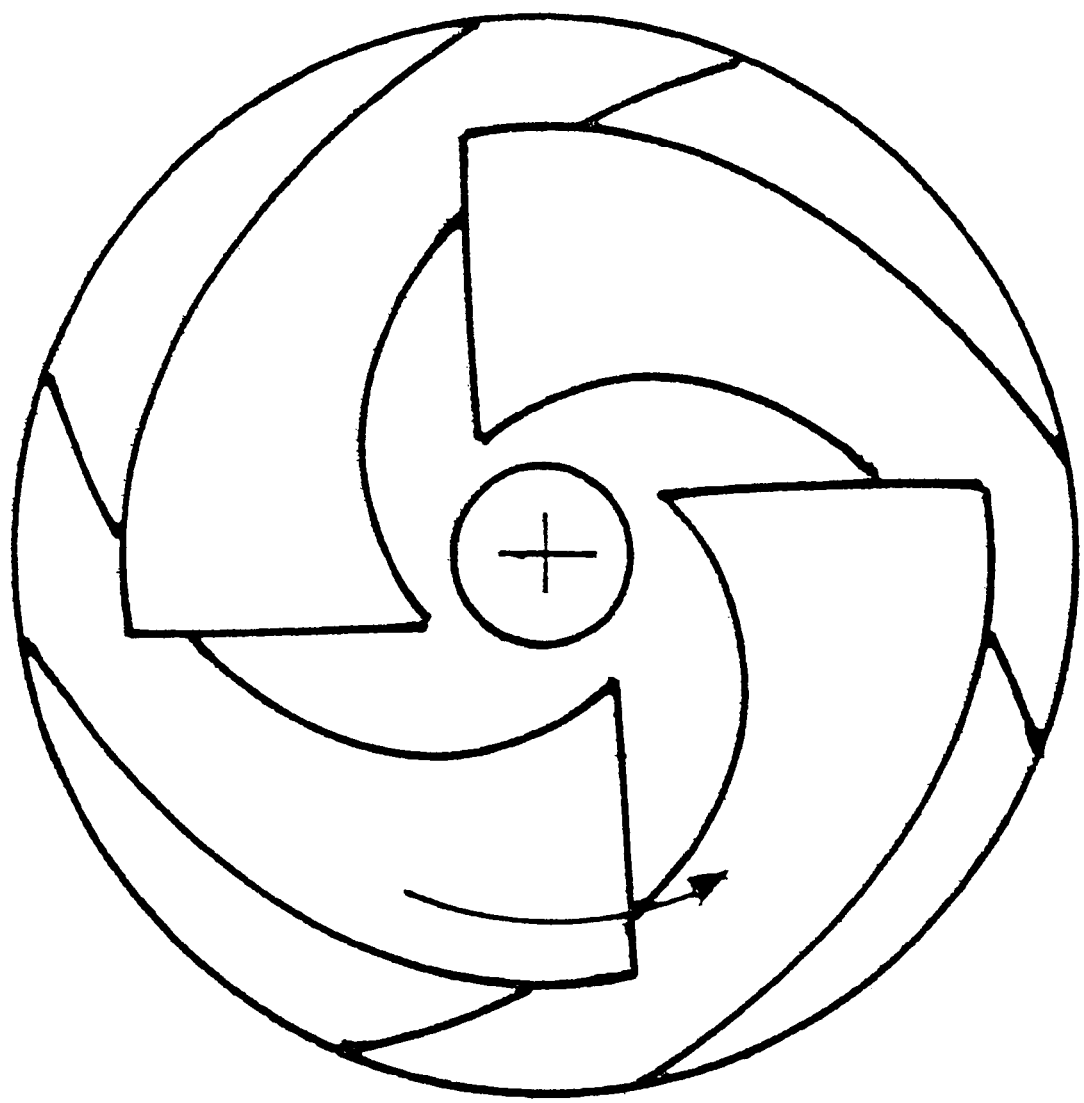
FIG. 4 shows the plane view of a semiopen radial vane impeller having forward-curved vanes.
Figure 5:
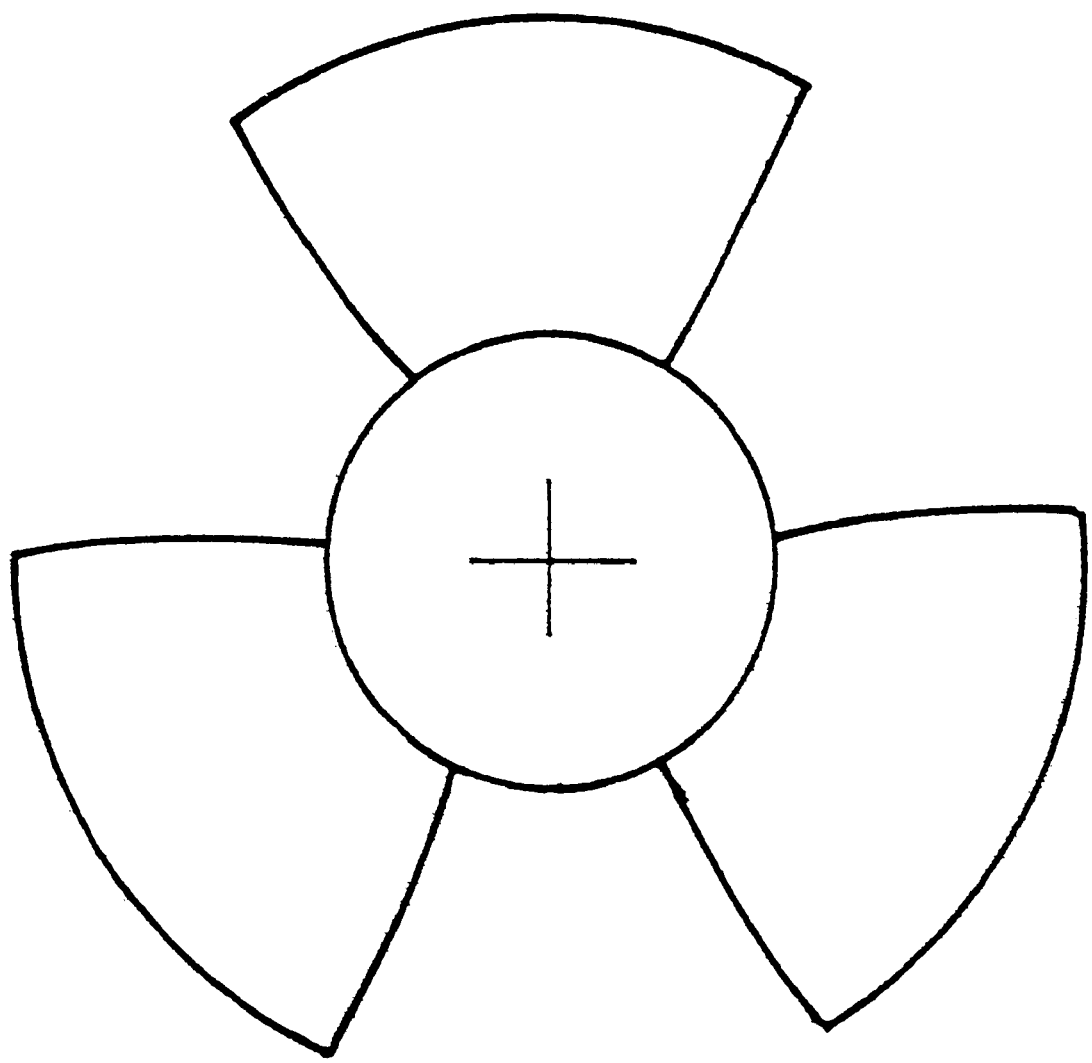
FIG. 5 shows spiral backwarded-curved vanes also applicable in radial impellers.

However, it is also possible in principle to use slightly forward-curved vanes (for example, as in FIG. 4), and also spiral, i.e. twisted into one another, backward-curved vanes whose blades project into the impeller inlet and capture the liquid to be conveyed like a ship's propeller (cf. for example, FIG. 5).

Figure 6A:
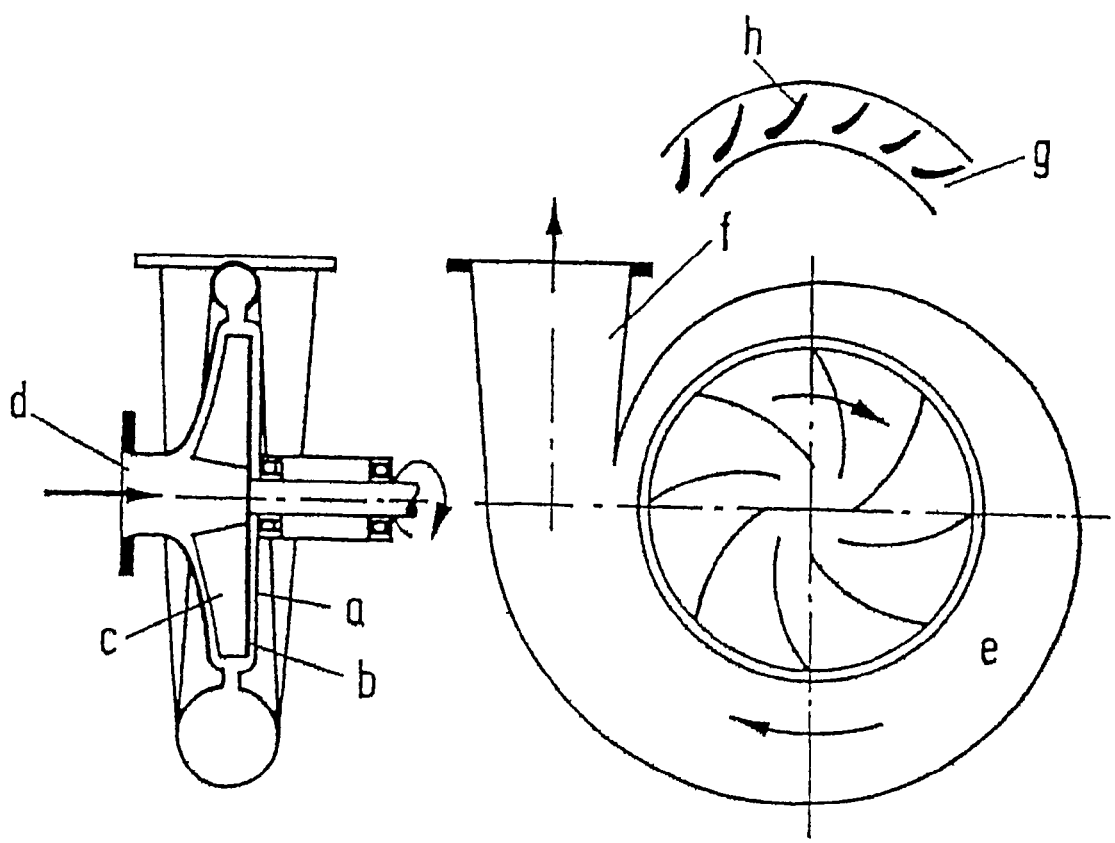
FIGS. 6 *a*) and *b*) illustrate the mode of function of a radial centrifugal pump with semiopen radial impeller.
Figure 6B:
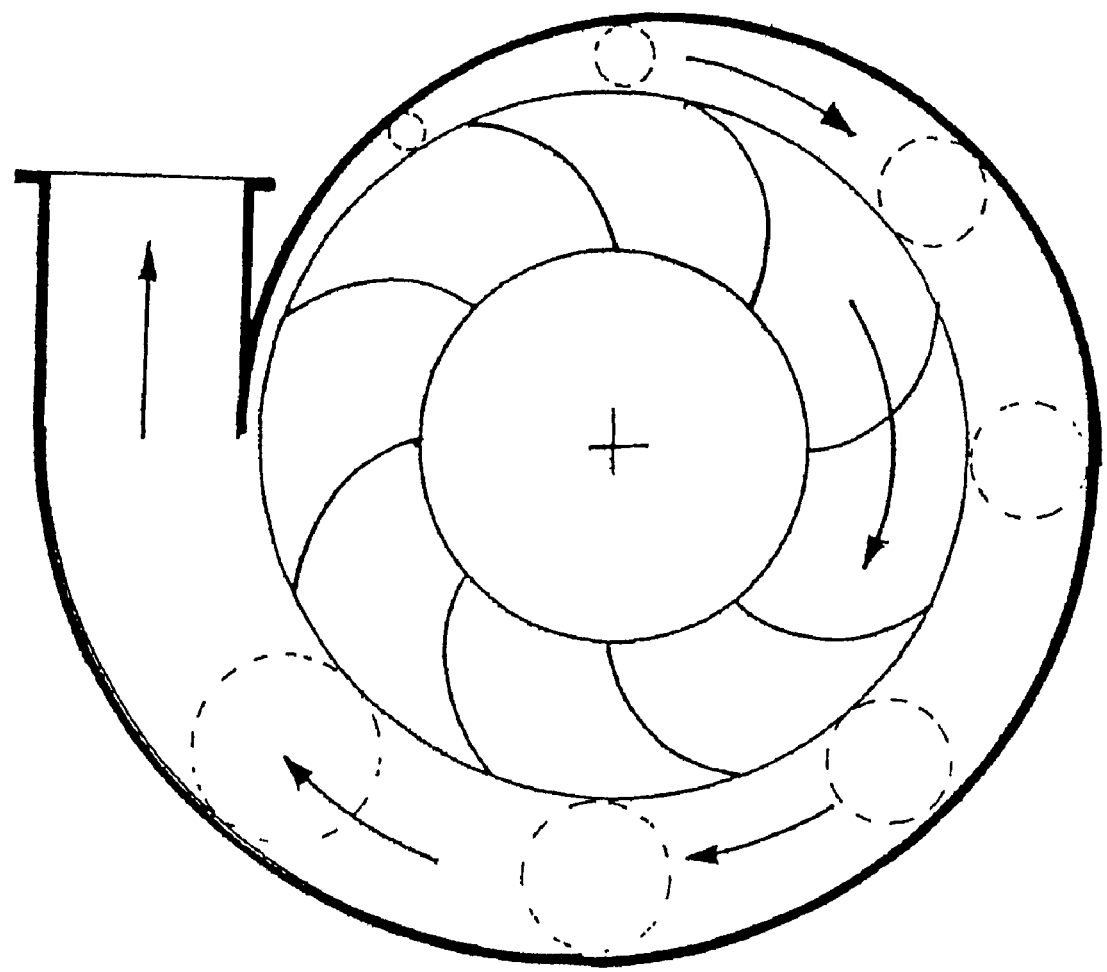

The mode of function of a radial centrifugal pump with semiopen radial impeller is illustrated by way of example in FIGS. 6a, 6b.

The radial centrifugal pump shown consists of the pump housing (a) and the semiopen impeller (b) rotating therein, which is provided with vanes (c). The liquid to be conveyed enters axially through the suction nozzle (d). It is deflected radially outward by the centrifugal force and is accelerated to high speed on this path by the impeller. The pump housing has the task of collecting the liquid to be conveyed from all vane channels, in order that it can be passed on through the pressure outlets (f). However, the pump housing simultaneously has the task of converting kinetic energy of the liquid to pressure. This generally exploits the fact that a cross-sectional enlargement lowers the speed of the liquid and thus brings about a rise in pressure. For cross-sectional enlargement, two constructions of the pump housing are customary. One embodiment is frequently that of a spiral housing.

Such a housing encloses the impeller in spiral form (e). The cross section widens in the direction toward the pressure outlet (see increasing circle radii in FIG. 6b).

Figure 7:
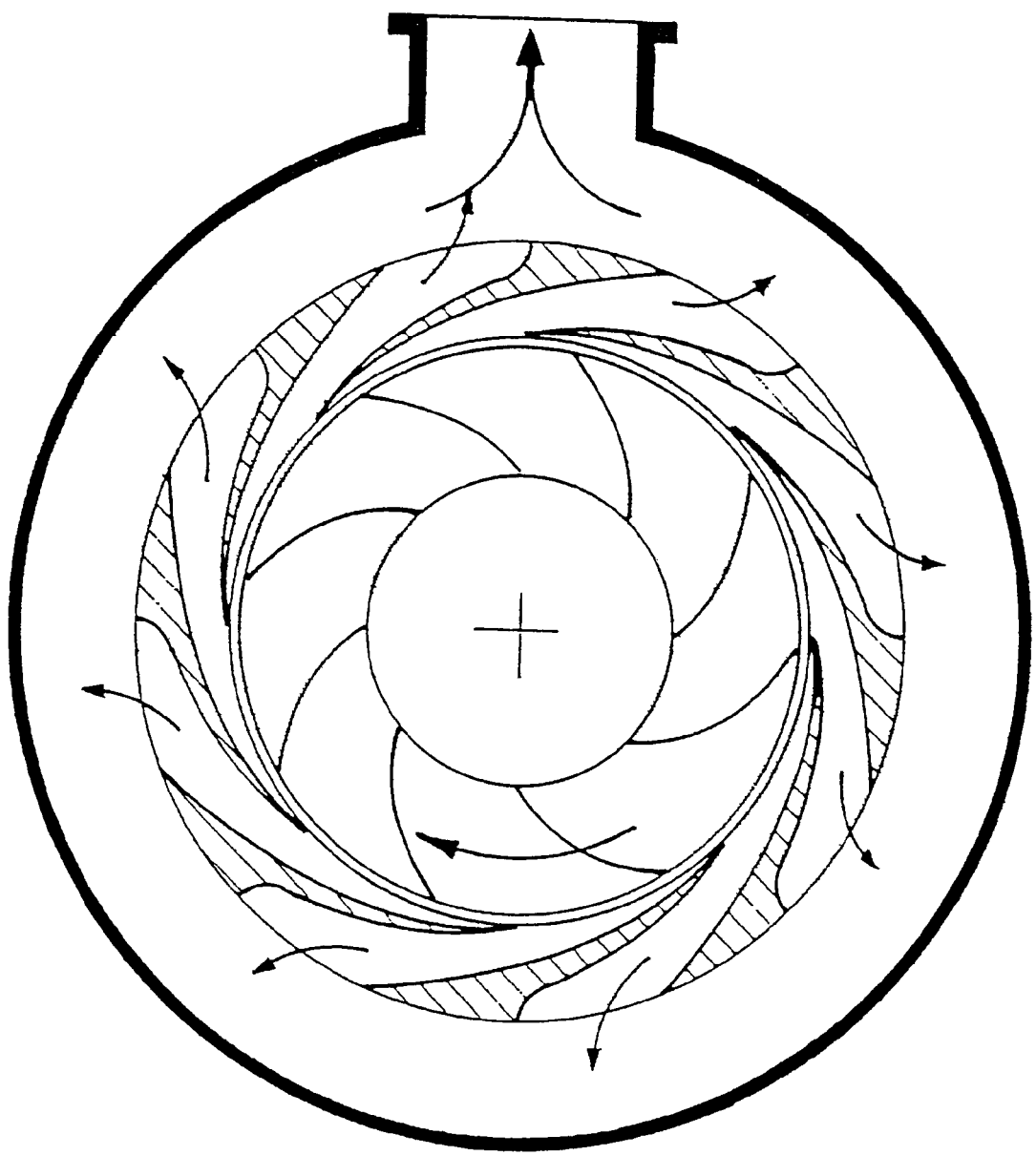
FIG. 7 shows a radial centrifugal pump having a fixed stator installed. In the stator, stator vanes are arranged, which, with respect to one another, form constantly widening channels in the outward direction.

The flowing liquid is slowed as a result, which means a simultaneous pressure increase. Instead of the spiral, particularly in multistage pumps, fixed stators (g) are also used. The stator is installed in the pump housing and configured as an annular space. It encloses the impeller. In the stator, stator vanes (h) are arranged, which, with respect to one another, form constantly widening channels in the outward direction (cf. also FIG. 7 in plan view). In this configuration, the liquid is not thrown directly into the pump housing, but first flows through the vane channels of the stator. As a result of the widening in flow direction, these in turn bring about a slowing of the flow rate and the pressure drop caused thereby. The direction of the stator channels is normally the opposite of the direction of the impeller channels and corresponds at the inner circumference of the stator to the direction of the exit velocity of the conveyed liquid from the impeller. It will be appreciated that it is also possible to use a combination of impeller and spiral housing. This means that the liquid to be conveyed is first collected in the stator before it can get into the spiral housing.

Figure 3:
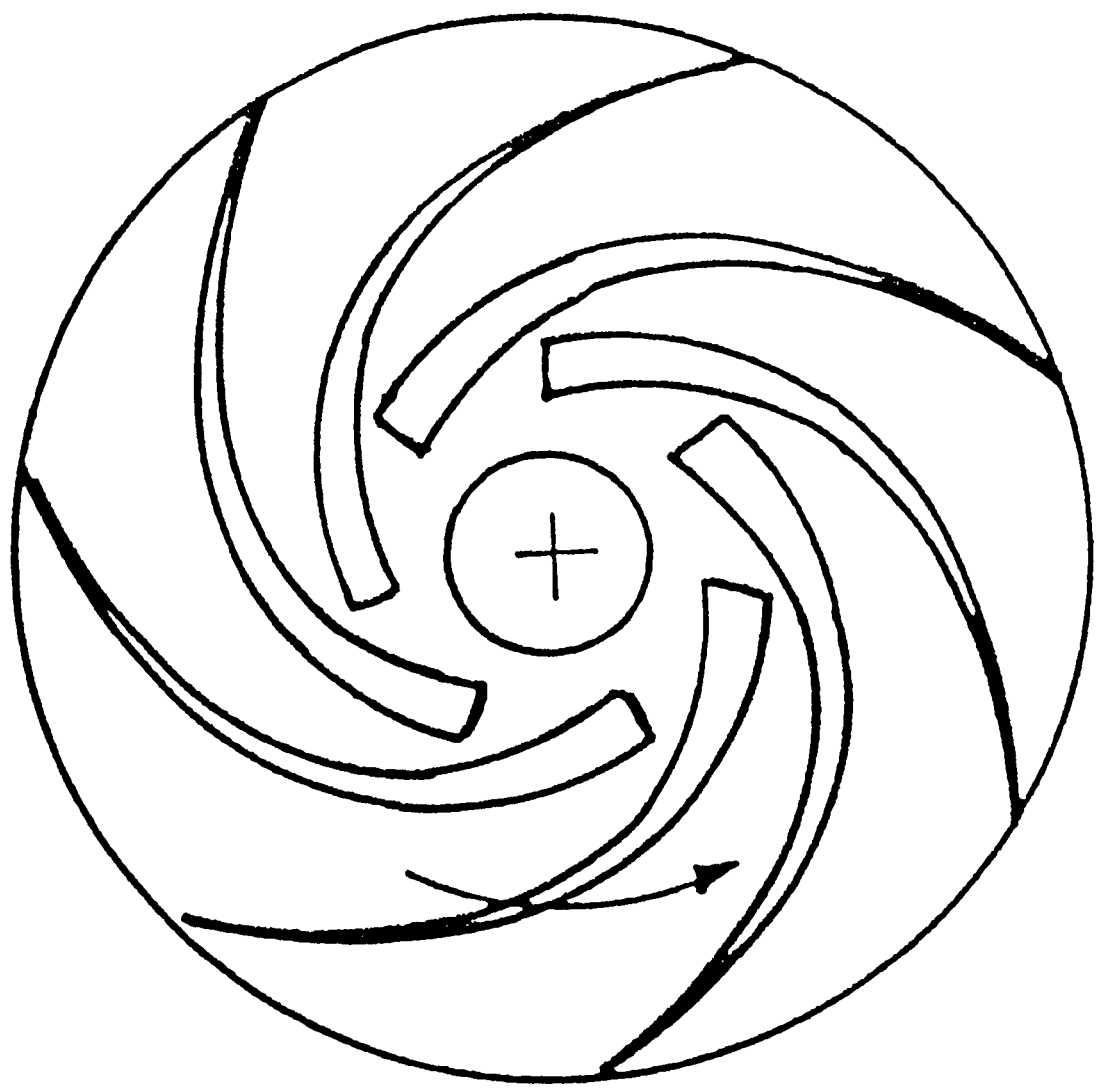
FIG. 3 shows the plan view of a semiopen radial vane impeller having backward-curved vanes.

While what has been described so far has essentially been just the pump space; the drive space will be discussed hereinafter. High-speed power machines, for example electric motors, internal combustion engines or steam turbines, drive the impeller in direct coupling. The coupling is accomplished by a drive shaft. The mounting thereof may be accommodated exclusively in the drive space, as shown by FIG. 3 of EP-A 1 092 874. Preferably in accordance with the invention, the pump space and the drive space are separated from one another by a separating space.

Advantageously, the separating space is filled with a barrier medium which consists of a barrier gas and/or of a barrier fluid and may be a different substance from the liquid to be conveyed or be identical thereto. Further advantageously the drive shaft is not mounted within the pump space. The pressure of the barrier medium is normally greater than the pressure in the pump space and than the pressure in the drive space. Moreover, it is appropriate in application terms that the section of the drive shaft which leads through the separating space bears, in both directions toward the pump space and toward the drive space, sliding elements which are connected firmly and imperviously to the drive shaft in each case and slide with sealing action on the inner walls of the separating space which are pierced by the drive shaft (principle of double-action (on both sides) sliding element (e.g. ring) seal).

In general, the pressure in the separating space is at least 1 bar greater than the pressure at the point opposite the sliding element in the pump space. Frequently, this pressure difference is >2 bar or >3 bar. Typically, this pressure difference will be ≦10 bar. When the barrier medium used in the process according to the invention is a gas, it is preferably an oxygen-comprising gas, since molecular oxygen has polymerization-inhibiting action on acrylic acid and esters thereof.

This polymerization-inhibiting action is displayed especially in connection with the polymerization inhibitors typically present in the liquid F, for example, phenothiazine or methoxyphenol. However, it will be appreciated that the liquid F in the process according to the invention may also comprise any other known polymerization inhibitor.

The oxygen content of such a barrier gas is preferably 3 to 21% by volume (for example, it is also possible to use cycle gas as the barrier gas).

In the case of liquids which are to be conveyed in accordance with the invention and whose flashpoint (determined to DIN EN 57) is <50° C., an oxygen content of a barrier gas of 4 to 10% by volume is very particularly preferred. When a barrier fluid is used in the process according to the invention (e.g. 2-ethylhexanol), it is preferably selected such that it is compatible with the liquid to be conveyed.

The barrier fluids preferred for the process according to the invention are mixtures of ethylene glycol and water or the two liquids alone.

Particular preference is given to those mixtures whose ethylene glycol content is 30 to 40% by weight. The ethylene glycol/water mixtures addressed exhibit outstanding viscosity behavior and are additionally found to be comparatively freezing-resistant under customary outside conditions. In the process according to the invention, barrier fluids are preferred over barrier gases. As sealing sliding elements, they typically comprise slip ring seals. These consist of a slip ring which is bonded firmly to the drive shaft and rotates with the drive shaft, and a slip ring fixed in the separating space inner wall.

A spring forces the slip ring against the opposite ring, normally with a prestress of 1 to 2 bar. In operation, it is supplemented by the elevated pressure of the barrier medium present between the slip ring seals. The elevated pressure of the barrier medium compared to the pressure on the pressure side of the pump prevents the liquid to be conveyed from escaping from the pump space.

Owing to the elevated pressure in the barrier medium, some barrier medium normally passes constantly into the conveyed liquid. In the case of a barrier fluid, this leakage rate may be 0.2 to 5 ml/h, for 1 m$^3$/h to 4000 m$^3$/h of conveyed flow. For barrier gases, the leakage rate based on the same conveyed flow is 12 to 150 ml (STP)/h of barrier gas. According to the invention, the leakage rate is appropriately replenished continuously from reservoir vessels.

The barrier medium, for example the barrier fluid, can also contribute to the lubrication of the sliding surfaces. Further details of the calculation and construction of axial slip ring seals can be found in E. Mayer: Berechnung and Konstruktion von axialen Gleitringdichtungen [Calculation and Construction of Axial Slip Ring Seals], Konstruktion 20, 213-219 (1968). It should also be emphasized at this point that, in this document, a bearing shall be understood to mean quite generally a machine element for bearing or guiding of machine parts moving relative to one another, which absorbs the forces which occur and dissipates them to the housing, component or foundation.

A radial centrifugal pump suitable in a particularly advantageous manner for the process according to the invention is the KSB CPKN-C1.V 200-400 radial centrifugal pump, from KSB Aktiengesellschaft in D-67227 Frankenthal (Pfalz), with a double-action slip ring seal and an ethylene glycol/water mixture as a barrier fluid.

However, in its standard version, the aforementioned radial centrifugal pump is supplied only with a closed radial impeller. For an inventive use of this pump, it is therefore necessary to remove the top plate from the impeller vanes beforehand (CPK=standard chemical pump; N=reinforced bearing seat for improved mounting of the drive shaft; C1=DIN material 1.4408, V=VDMA materials key, 200=nominal width on pressure side in mm, 400=impeller diameter in mm).

The process according to the invention is suitable, among other cases, in that of liquids F which comprise Michael adducts which are formed in the course of preparation of esters of acrylic acids with mono- or dihydric alcohols (having one or two hydroxyl groups) (e.g. $C_1$- to $C_{10}$-, or to $C_8$-alcohols), especially alkanols (by direct reaction of the acrylic acid with the particular alcohol). This is especially true when the particular alcohol is a $C_1$- to $C_{10}$-alkanol (e.g. is a $C_4$- to $C_{10}$-alkanol, or a $C_4$- to $C_8$-alkanol). These esters of acrylic acid include, for example, hydroxyethyl acrylate, 4-hydroxybutyl acrylate, hydroxypropyl acrylate, methyl acrylate, n-butyl acrylate, isobutyl acrylate, tert-butyl acrylate, ethyl acrylate, 2-propylheptyl acrylate and 2-ethylhexyl acrylate.

However, the process according to the invention can also be employed in the case of liquids F, which comprise Michael adducts which are formed in the course of preparation of esters of acrylic acid with amino alcohols, for example aminoethanol, N-methylaminoethanol and N,N-dimethylaminoethanol (by direct reaction of the acrylic acid with the particular alcohol).

Liquids F comprising Michael adducts of this type are disclosed, for example, in documents EPA 780 360, DE-A 197 01 737, DE-A 2339519, DE-B 1279015 and EP-A 1 357 105 (including the formation thereof).

They are obtained in a simple manner when, for example, in a generally acid-catalyzed esterification of acrylic acid with alcohols (e.g. monohydric alkanols), the unconverted starting materials and the acrylic esters formed, which are normally more volatile compared to the relevant Michael adducts, are separated by rectification from the resulting product mixture, such that the Michael adducts are enriched in the rectification bottoms and this bottoms liquid constitutes a typical liquid F for treatment in accordance with the invention after it has been withdrawn from the rectification column. This esterification may have been performed either in a solvent or without addition of solvent.

In general, liquids F for treatment in accordance with the invention, including those whose Michael adducts present therein have been formed in the course of preparation of acrylic acid, comprise at least ($\geqq$) 20% by weight, or at least 30% by weight, or at least 40% by weight (in each case of their weight) of Michael adducts. In general the above content of Michael adducts in liquids F for treatment in accordance with the invention (to be subjected to a process according to the invention) is, however, $\leqq$90% by weight, usually $\leqq$80% by weight and often $\leqq$70% by weight or even $\leqq$60% by weight (liquids F for treatment in accordance with the invention are generally analyzed by means of GC and HPLC).

Typically, a liquid F to be subjected to a process according to the invention, whose Michael adducts present therein have been formed in the course of preparation of an ester of the acrylic acid (for example of a $C_1$- to $C_{10}$- or to $C_8$-alkanol or alcohol or of a $C_4$- to $C_8$-alkanol or alcohol, or of a $C_1$- to $C_4$-alkanol or alcohol), may have, for example, the following contents:

| | |
|---|---|
| 1 to 30% by weight | of acrylic esters, |
| 40 to 80% by weight | of Michael adducts, and, as the remainder, essentially polymerization inhibitor (typically 0.1 to 2% by weight) and free-radical polymer (generally at least 15% by weight) of the acrylic acid and of the acrylic ester. |

In general, the Michael adducts consist to an extent of at least 50% by weight of their total weight of Michael adducts of the general formula III.

Frequently, dissociation catalyst is also added to a liquid F to be subjected to a process according to the invention prior to the redissociation, in order to lower that temperature at which redissociation already proceeds to a significant extent. Useful such redissociation catalysts include, for example, mineral acids, for example sulfuric acid and phosphoric acid, organic acids other than acrylic acid, for example alkyl- or arylsulfonic acids, such as methanesulfonic acid or p-toluenesulfonic acid. It is also possible to add amines, as described, for example, by DE-A 10 2006 062 258. It is possible in the process according to the invention to use all dissociation catalysts known in the literature (cf., for example WO 2004/035514, EP-A 780 360, EP-A 1 357 105, DE-A 2339519, DE-B 1 279 015, WO 2004/035514, JP-A 178949, DE-A 197 01 737).

Based on its weight, free of dissociation catalysts, liquid may comprise, for example, 0.01-20% by weight of added dissociation catalysts before it is subjected to a process according to the invention.

Liquids F, which comprise Michael adducts which have been formed in the course of preparation of acrylic acid are obtained, for example, in processes for preparing acrylic acid in which an acrylic acid-comprising product gas mixture obtained by catalytic gas phase partial oxidation of a $C_3$-precursor compound of acrylic acid, optionally after preceding cooling, is fractionally condensed ascending into itself with side draw removal of crude acrylic acid in a separating column provided with separating internals, and the liquid formed, which comprises Michael adducts of acrylic acid, is conducted continuously out of the bottom of the condensation column and fed as liquid F to the redissociation of the Michael adducts of acrylic acid present therein (cf. for example DE-A 10 2007 004 960, WO 2004/035514, DE-A 10 2006 062 258 and German Application 10 2008 001 435.4).

Typically, such a liquid F for treatment in accordance with the invention, including any (re)dissociation catalysts added prior to a performance of the process according to the invention, may comprise:

| | |
|---|---|
| 10 to 50% by weight | of Michael acrylic acid oligomers (Michael adducts), |
| at least 40% by weight | of free-radical acrylic acid polymer, |
| up to 25% by weight | of monomeric acrylic acid, |
| up to 2% by weight | of polymerization inhibitor, and |
| up to 15% by weight | of other compounds. |

Frequently, such liquids F also comprise:

| | |
|---|---|
| 10 to 50% by weight | of Michael acrylic acid oligomers (Michael adducts), |
| 40 to 80% by weight | of free-radical acrylic acid polymer, |
| 5 to 20% by weight | of monomeric acrylic acid, |
| 0.1 to 2% by weight | of polymerization inhibitor, and |
| 1 to 15% by weight | of other compounds. |

They may, however, also comprise:

| | |
|---|---|
| 10 to 40% by weight | of Michael acrylic acid oligomers (Michael adducts), |
| 50 to 70% by weight | of free-radical acrylic acid polymer, |
| 5 to 15% by weight | of monomeric acrylic acid, |
| 0.1 to 1% by weight | of polymerization inhibitor, and |
| 1 to 15% by weight | of other compounds; |
| or: | |
| 15 to 35% by weight | of Michael acrylic acid oligomers, |
| 50 to 70% by weight | of free-radical acrylic acid polymer, |
| 5 to 15% by weight | of monomeric acrylic acid, |
| 0.1 to 1% by weight | of polymerization inhibitor, and |
| 1 to 15% by weight | of other compounds. |

Frequently, in the liquids F, 40 to 60% by weight of the Michael acrylic acid oligomers present therein are only Michael acrylic acid dimers and 15 to 30% by weight are Michael acrylic acid trimers.

It will be appreciated that liquids F to be subjected to the process according to the invention may also arise when the acrylic acid present in the product gas mixture of the heterogeneously catalyzed gas phase partial oxidation is converted to the liquid phase by absorption into an absorbent and the acrylic acid is subsequently removed from the absorbate by means of rectificative and/or crystallizative separation processes, as disclosed, for example, by DE-A 103 36 386 and DE-A 29 01 783.

In general, liquids F for treatment in accordance with the invention, based on their weight, comprise at least 10 ppm by weight, frequently at least 50 ppm by weight and in many cases at least 150 ppm by weight of polymerization inhibitor. In general, the content of polymerization inhibitors in liquids F, on the same basis, is $\leq 1\%$ by weight, or $\leq 0.5\%$ by weight. In addition to phenothiazine and/or hydroquinone monomethyl ether and conversion products thereof, useful such polymerization inhibitors also include compounds such as alkylphenols (e.g. o-, m- or p-cresol (methylphenol)), hydroxyphenols (e.g. hydroquinone), tocopherols (e.g. o-tocopherol) and N-oxyls such as hydroxy-2,2,6,6-tetramethylpiperidine-N-oxyl, and the other inhibitors known in the literature.

The constituents of liquids F other than acrylic acid, the esters of acrylic acid and the Michael adducts are primarily compounds which are higher-boiling than acrylic acid and esters thereof at standard pressure.

If required, they may also comprise added surfactants, as described, for example, in German application 10 2008 001 435.4.

Useful separating columns K for the process according to the invention are, in principle, all types of rectification columns known per se.

These are all columns comprising separating internals, useful separating internals including, for example, structured packings, random packings, and/or trays. The separating internals pursue the purpose of increasing the exchange area between gas phase ascending in the separating column K and liquid descending in the separating column K, thus improving both the mass transfer and the heat transfer between the two phases. They are permeable both to gas ascending in the separating column K and liquid descending in the separating column K.

Preferably, in accordance with the invention, the separating column K comprises only trays and/or structured packings. The trays used are advantageously dual-flow trays, and the separating column K particularly advantageously comprises exclusively dual-flow trays as separating internals.

In this document, dual-flow trays are understood to mean plates with simple passages (holes, slots, etc.). The gas ascending in the separating column K and the liquid descending in the separating column meet flowing in opposite directions through the same passages. The cross section of the passages is adjusted in a manner known per se to the loading of the separating column K. When it is too small, the ascending cleavage gas flows through the passages at such a high rate that the liquid descending in the separating column K is essentially entrained without separating action. When the cross section of the passages is too great, ascending cleavage gas and descending liquid move past one another essentially without exchange, and the tray is at risk of running dry. Typically, dual-flow trays have no drainpipe which connects them to the next tray. Of course, any dual-flow tray can conclude flush with the walls of the rectification column. However, it may also be joined thereto via connecting elements. With increasing loading of the rectification column, dual-flow trays run dry, unlike hydraulically sealed crossflow trays.

The passages of the dual-flow trays are preferably circular holes with a homogeneous circle diameter within the tray. The latter is appropriately 10 to 30 mm. In the upper part of the column it is advantageously 10 to 20 mm, or 10 to 15 mm, and in the lower part of the separating column K it is advantageously 20 to 30 mm. The circular holes are preferably arranged homogeneously in strict triangular pitch over an individual dual-flow tray (cf. DE-A 102 30 219). In addition, the punching burr of the passages punched into the dual-flow trays preferably points downward in the separating column K. Typically, the dual-flow trays in the separating column K are arranged equidistantly. Typically, the tray separation is 300 to 500 mm. Also favorable is a tray separation of 400 mm.

The feed point I, at which the liquid F is conducted into the separating column K is, in accordance with the invention, above the lowermost separating internals in the separating column K (FIG. 10). In the case of a tray column, the feed point I is thus above the lowermost tray.

When the separating column K is a column with purely structured packing, the feed point I is above the lowermost structured packing element.

A separating column K with purely dual-flow trays may, in the process according to the invention, comprise up to 60 dual-flow trays or more. Advantageously, they have an orifice ratio (the ratio D:U formed from the proportion of tray area which is permeable to the cleavage gas (D) and the total area of the tray (U) of 10 to 20%, preferably of 10 to 15%.

Advantageously, in accordance with the invention, the feed point I, in the case of a column with purely dual-flow trays (e.g. with $\geqq 40$ equidistant dual-flow trays) is in the region of the fourth to tenth dual-flow tray viewed from the bottom upward. Appropriately in application terms, the feed temperature $T^Z$ of the liquid F at the feed point I corresponds to that temperature which the liquid descending in the separating column K has at this point. Advantageously, the two aforementioned temperatures deviate from one another by not more than 10% (based on the arithmetic mean). Appropriately in application terms, the separating column K, just like its input and output lines, is thermally insulated from the environment.

In general, separating columns K with 2 to 25 theoretical plates are sufficient. A theoretical plate is understood to mean that three-dimensional unit of the separating space comprising separating internals in the separating column K which brings about a mass enrichment according to the thermodynamic equilibrium without energy loss.

The feed point I of a separating column K used in accordance with the invention is preferably in the region of the second to eighth theoretical plate viewed from the bottom upward.

The reflux liquid for the separating column K can be obtained by direct and/or indirect cooling of the gas stream G flowing into the (to the) top space of the separating column K. Advantageously in accordance with the invention, the method of direct cooling is employed.

To this end, in the simplest manner, the gas stream G flowing through the uppermost separating internal of the separating column K into the top space above it is fed to a quench apparatus which may be integrated, for example, into the top space (in this case, the top space is separated from the separating space, for example, by means of a chimney tray; bottom space and top space do not comprise any separating internals). In principle, the quench apparatus may, however, also be spatially separated from the separating column K. Such a quench apparatus used may be any apparatus known for this purpose in the prior art, (for example, spray scrubbers, Venturi scrubbers, bubble columns or other apparatus with sprayed surfaces), preference being given to Venturi scrubbers or spray coolers. Advantageously, a cocurrent apparatus (for example one with a baffle plate nozzle) is used. For indirect cooling of the quench liquid, it is typically conducted through an (indirect) heat transferer or heat exchanger. In this regard, all common heat transferers or heat exchangers are suitable. Preferred examples include tube bundle heat exchangers, plate heat exchangers and air coolers. Suitable cooling media are air in the case of the corresponding air cooler, and cooling liquids, especially water (e.g. surface water), in the case of the other cooling apparatus. Appropriately in application terms, the quench liquid used is a portion of the condensate formed in the course of quenching. The other portion of the condensate formed in the course of quenching is normally recycled essentially as reflux liquid to the uppermost separating internal in the separating column K (if required, a portion of the condensate can also be discharged). Of course, the condensation can also be performed exclusively with indirect heat exchangers integrated into the top space and/or separate from the top space, by conducting the gas stream G through them.

Advantageously in application terms, the separating column K is operated with polymerization inhibitors. The polymerization inhibitors of this type used for this purpose may in principle be all polymerization inhibitors known in the prior art for acrylic monomers. Examples of these include phenothiazine (PTZ) and p-methoxyphenol (MEHQ).

Frequently, these two are employed in combination. Appropriately, they are added to the reflux liquid dissolved in pure redissociation product. MEHQ is preferably metered in as a melt.

The feed point II (this is understood to mean the point in the bottom space of the separating column K at which the substream II exits from the feed line into the bottom space) in the process according to the invention is present below the lowermost separating internal of the separating column K and above the level S of the bottoms liquid (of the liquid effluxing into the bottom space of the separating column K). Advantageously in accordance with the invention the level S (of the bottoms liquid) of the liquid effluxing into the bottom space is adjusted such that it is less than 40%, preferably less than 30% and more preferably less than 20% of the distance A. In general, the level S will, however, not be less than 5% of the distance A (safe liquid level).

Figure 1:
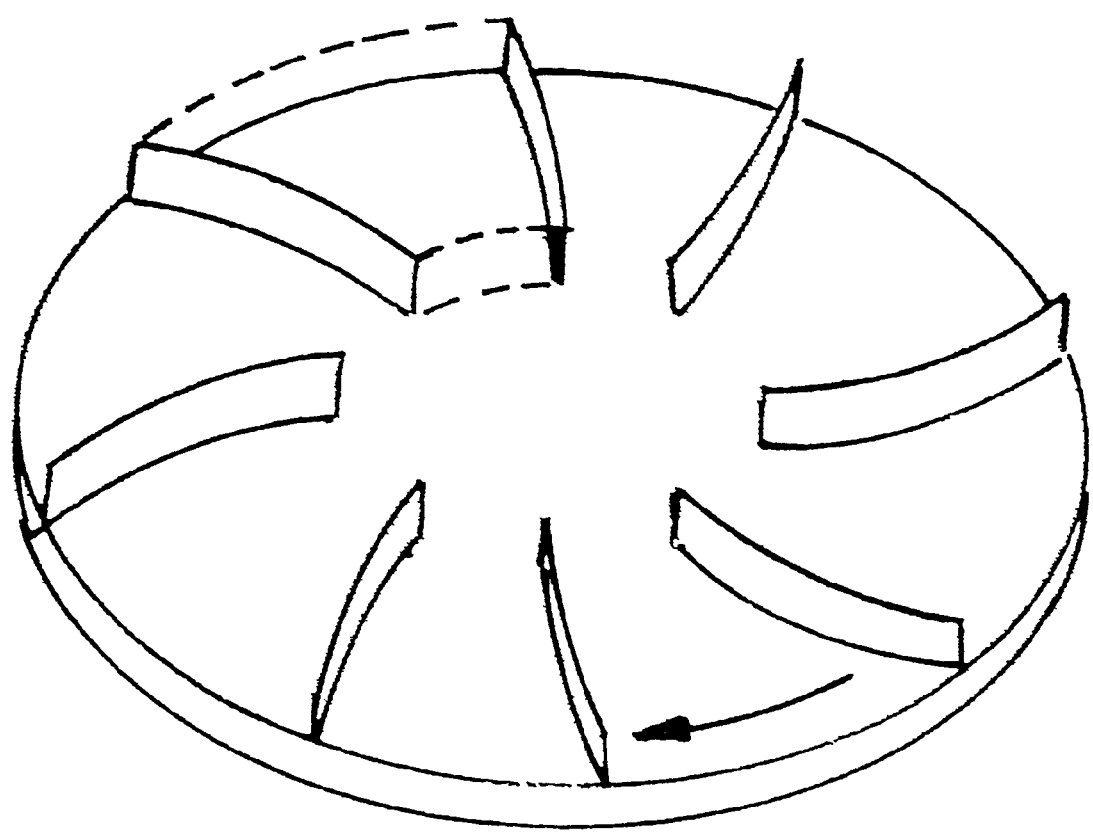
FIG. 1 shows a semiopen radial impeller.
Figure 2:
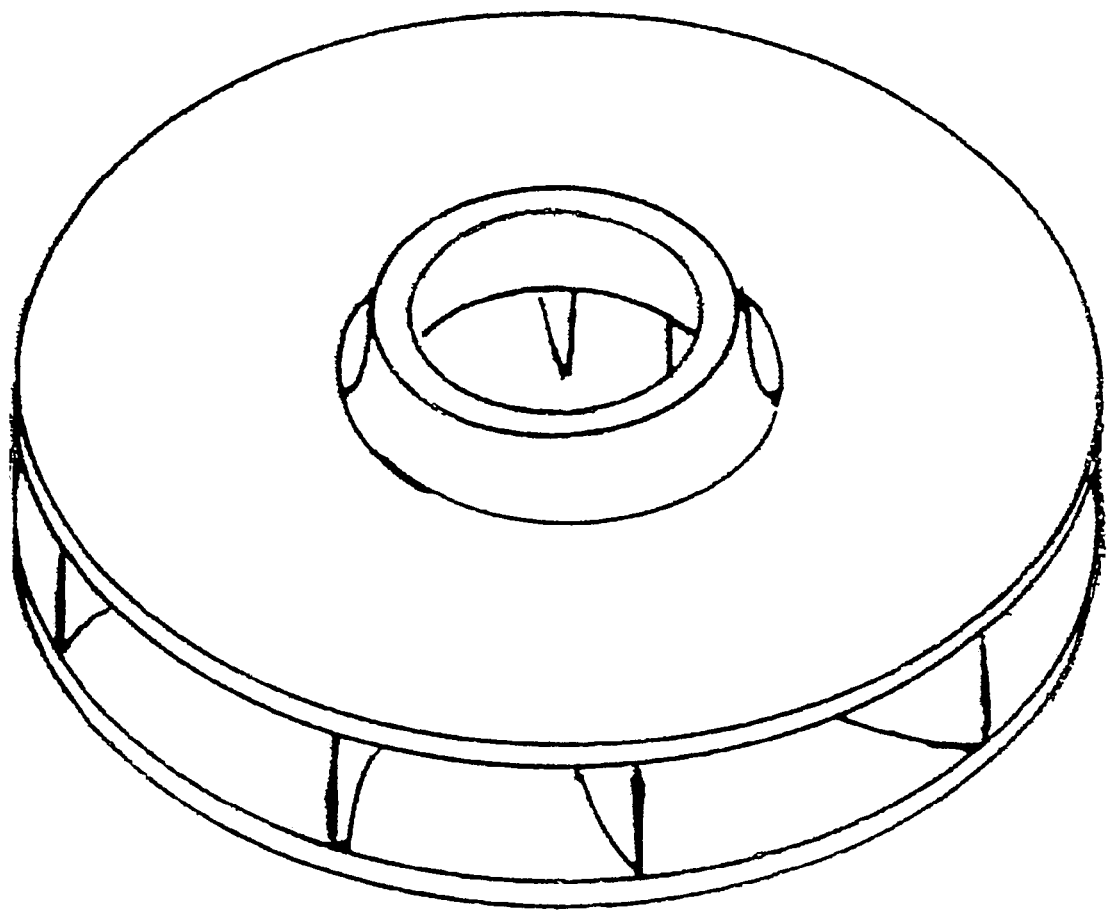
FIG. 2 shows a closed radial impeller.

Advantageously, in accordance with the invention, this safe level is achieved with a small bottoms liquid volume by mounting displacement bodies in the bottom space or tapering the bottom space toward its lower end (cf. FIG. 6 of DE-A 103 32 758 or else EP-A 1 095 685, and also FIG. 1 of DE-A 10 2004 015 727).

Particularly advantageously, the bottom space is tapered toward its lower end and the level S of the liquid effluxing into the bottom space (the level of the bottoms liquid) is within the section of the bottom space in which the bottom space is tapered (i.e. in the section in which it has a reduced internal diameter).

In general, the feed point II in the process according to the invention is at least 0.25·A above the level S of the bottoms liquid (above the liquid level of the bottoms liquid).

According to the invention, the substream II is recycled into the bottom space of the separating column K in such a way that the substream II in the bottom space of the separating column K is not directed toward the bottoms liquid (i.e. the extension of the flow vector of that flow with which the substream II exits from the appropriate feed line into the bottom space does not meet the bottoms liquid), but a material object other than the bottoms liquid (for example the wall of the bottom space, a baffle plate, etc.).

In a simple manner, the aforementioned inventive condition can be achieved by virtue of the substream II flowing horizontally into the bottom space (for example, via a simple feed stub).

Advantageously, however, the substream II flows into the bottom space of the separating column K from a line A which is conducted into the bottom space and whose exit orifice in the bottom space does point downward but is not directed toward the bottoms liquid but toward a baffle device A (directed to a flow distributor) which is mounted in the bottom space above the level S of the bottoms liquid, and which deflects the substream II upward when it hits the baffle device (cf., for example, FIG. 1 of DE-A 10 2004 015 727).

When "stripping gas" is used in the separating column K as an entraining agent (entraining gas or else support gas) for the redissociation products (dissociation products), it is likewise conducted, in the process according to the invention, into the bottom space of the separating column K above the level S of the bottoms liquid and below the lowermost separating internals of the separating column K (and flows from there into the top space of the separating column K). This is again done in such a way that the gas stream in the bottom space of the separating column K is not directed toward the bottoms liquid (i.e. the extension of the flow vector with which the gas stream exits from the corresponding feed line into the bottom space does not meet the bottoms liquid).

This can be achieved in a simple manner by virtue of the stripping gas stream flowing horizontally into the bottom space (for example via a simple feed stub). The feed point for this purpose may be either above or below the feed point II.

Advantageously, however, a stripping gas stream flows into the bottom space of the separating column K from a line B which is conducted into the bottom space and whose exit orifice in the bottom space points downward but is not directed toward the bottoms liquid but toward a baffle device B (directed toward a flow distributor) which is mounted in the bottom space above the level S of the bottoms liquid, and deflects the stripping gas stream upward when it hits the baffle device (cf., for example, FIG. 1 of DE-A 10 2004 015 727).

Appropriately in application terms, the substream II is conducted into the bottom space of the separating column K through a line A whose exit orifice A is directed toward a baffle device A and, simultaneously, a stripping gas stream through a line B whose exit orifice B is directed toward a baffle device B. The baffle device A and, with it, the exit orifice A too may be either above or below the baffle device B and the corresponding exit orifice B. Preferably in application terms, line A surrounds line B (both lines form (preferably thermally insulated from one another) a "coaxial double tube") and exit orifices A and B are present essentially at the same height, and the baffle device B is identical device to the baffle device A.

For reasons of polymerization inhibition, the stripping gas preferably comprises molecular oxygen. Useful examples include air, oxygen-depleted air and/or cycle gas. Cycle gas is understood to mean the residual gas which remains when the acrylic acid from the product gas mixture of the heterogeneously catalyzed gas phase partial oxidation of a $C_3$ precursor compound (for example, propene, propane, acrolein, glycerol) employed to prepare acrylic acid is converted to the liquid state by absorption with a liquid absorbent or by fractional condensation (cf. for example WO 2004/035514, DE-A 103 32 758, DE-A 10 2007 004 960). The predominant amount of this residual gas is recycled into the partial oxidation in circulation, in order to dilute the reaction gas mixture.

In general, an aqueous phase is also condensed out of the aforementioned residual gas prior to its use as a stripping gas and generally comprises residual amounts of acrylic acid (acid water), which can be removed from this aqueous phase by extraction with an organic extractant into the resulting extract. Prior to use of the residual gas as stripping gas in the process according to the invention, the residual gas may also have been used to strip the acrylic acid out of the aforementioned extract (cf. DE-A 10 2007 004 960). Normally, the stripping gas is supplied with a temperature which is below $T^{SU}$ and above 100° C., in some cases above 150° C.

Based on 1 kg of liquid F supplied at the feed point I per hour, the stripping gas stream supplied may, for example, be 1 to 100 kg/h. Stripping gas is used especially when the circulation heat exchanger UW is a forced circulation flash heat exchanger.

The metered addition of stripping gas allows the partial pressure of the (re)dissociation products in the separating column K to be reduced in a manner corresponding to that of applying reduced pressure.

When no stripping gas is supplied to the separating column K in the process according to the invention, a working pressure which is advantageously below 1 bar (and is, for example, 100 mbar) is employed at the top of the column.

When a stripping gas is used, the working pressure at the top of the separating column K is generally at a pressure of >1 to 3 bar, preferably 1.5 to 2.5 bar.

The temperature $T^{SU}$ of bottoms liquid present in the bottom space with the level S is generally in the range from 130 to 250° C., frequently 150 to 190° C. and in many cases 160 to 180° C.

The difference $T^{RS}-T^{SU}$ in the process according to the invention will generally be at least 2° C., preferably at least 5° C. or at least 10° C. Normally, the aforementioned temperature difference will, however, be $\leq 100°$ C., frequently even $\leq 80°$ C. and often $\leq 50°$ C. In relative terms, the two temperatures in the process according to the invention should be selected such that the redissociation rate in the cleavage reactor is greater than the high boiler formation rate in the bottom of the separating column K.

In the case of an indirect circulation heat exchanger UW for use in accordance with the invention, the heat transfer is not effected by direct contact, forced by mixing, between fluid heat carrier and liquid mixture to be heated. Instead, the heat is transferred indirectly between the fluids separated by a separating wall. The separating area of the heat transferer (heat exchanger) which is active for heat transfer is referred to as the heat exchange or transfer area, and the heat transfer follows the known laws of thermal conduction.

It is essential in accordance with the invention that, in the process according to the invention, both the fluid heat carrier and the liquid F flow through the indirect circulation heat exchanger UW. In other words, both flow into the heat exchanger and then back out again (one flows through the at least one primary space and the other through the at least one secondary space).

Useful fluid heat carriers for the process according to the invention in principle include all possible hot gases, vapors and liquids.

The primary example thereof is steam, which may be at different pressures and temperatures. It is frequently favorable when the steam is condensed as it flows through the indirect heat exchanger (saturated steam).

Useful alternative fluid heat carriers are oils, melts, organic liquids and hot gases. Examples thereof are silicon compounds such as tetraaryl silicate, diphenyl-comprising mixture of 74% by weight of diphenyl ether and 26% by weight of diphenyl, the azeotrope of diphenyl and diphenyl ether, chlorinated noncombustible diphenyl, and also mineral oils and pressurized water.

The difference ($T^W-T^{SU}$) between that temperature $T^W$ with which the fluid heat carrier enters the at least one primary space of the circulation heat exchanger UW in the course of performance of the process according to the invention, and that temperature $T^{SU}$ with which the at least one substream I essentially enters the at least one secondary space of the same circulation heat exchanger UW may, for example, be 1 to 150° C., frequently 5 to 100° C., or 10 to 80° C., in many cases 20 to 60° C., or preferably 15 to 35° C.

Indirect circulation heat exchangers suitable for the process according to the invention are especially double tube heat transferers, tube bundle heat transferers, ribbed tube heat transferers, spiral heat transferers or plate heat transferers. Double tube heat transferers consist of two tubes with one inside the other.

A plurality of these double tubes may be combined to tube walls. The inner tube may be smooth or provided with ribs to improve the heat transfer. In individual cases, it is also possible for a tube bundle to represent the inner tube. The fluids undergoing heat transfer may move in cocurrent or in countercurrent. Appropriately, in accordance with the invention, the liquid F is conveyed upward in the inner tube, and hot steam flows, for example, downward in the annular space.

Particularly suitable circulation heat exchangers UW for the process according to the invention are tube bundle heat transferers. They consist normally of a self-contained wide outer tube which surrounds the numerous smooth or ribbed transferer tubes of small diameter, which are secured to tube plates.

The distance from tube center to tube center of the bundled tubes is, appropriately, in application terms, 1.3 to 2.5 times the outer tube diameter. The large specific heat exchange area which arises—as exchange area per unit of the space required—is an advantage of the tube bundle heat transferer. The tube bundle heat transferers arranged vertically or horizontally differ in aspects including the tube configuration. The transferer tubes may be straight, bent in a U shape or configured as a multiple spiral tube bundle.

The at least one substream I to be heated in accordance with the invention flows, preferably in accordance with the invention, within the transferer tubes (in principle, it may also flow in the space surrounding the transferer tubes, and the heat carrier within the transferer tubes). The fluid heat carrier (preferably saturated steam) flows, appropriately, in accordance with the invention, outside the transferer tubes. Guide plates for better conduction of the fluid heat carrier in the outer space are appropriate in accordance with the invention and generally serve the additional purpose of supporting the transferer tubes. The guide plates generally increase the flow rates in the outer space and hence, among other parameters, the heat transfer coefficients. In the outer space, the flow advantageously runs at right angles to the transferer tubes. According to the flow direction of the outer space fluid in relation to the transferer tubes, it is possible to distinguish, for example, longitudinal flow, crossflow and transverse flow tube bundle heat transferers. In principle, the fluid heat transferer can also be moved in a meandering manner around the transferer tubes and only viewed over the tube bundle heat exchanger be conducted in cocurrent or countercurrent to the liquid mixture to be heated in accordance with the invention. Spiral tube bundle heat transferers generally also utilize the advantages of crossflow. From position to position, the tubes alternate from right-handed to left-handed spirals. The outer space fluid flows in countercurrent to the tube fluid and flows around the spiral tubes in crosscurrent.

In the single flow tube bundle heat transferer, the at least one substream I to be heated in accordance with the invention moves through all transferer tubes in the same direction.

Multiflow tube bundle heat transferers comprise tube bundles divided into individual sections (in general, the individual sections comprise an identical number of tubes). Dividing walls divide chambers which adjoin the tube plates (through which the transferer tubes are conducted with sealing and to which they are secured) into sections, and divert the at least one substream I entering the chamber part from one section into a second section and hence back. The at least one substream I to be heated in accordance with the invention, according to the number of sections, flows through the length of the tube bundle heat transferer more than once (twice, three times, four times etc.) with high speed in alternating direction (two-flow, three-flow, four-flow, etc. tube bundle heat transferers). Heat transfer coefficient and exchange length increase correspondingly.

Plate heat transferers (plate heat exchangers) are normally composed in the manner of filter presses, generally of corrugated or otherwise profiled plates (generally of graphite or metal, for example stainless steel) provided with channels for the liquid heat carrier and the liquid mixture to be heated, in compact design. The two heat-exchanging fluids then flow in cocurrent, countercurrent and/or crosscurrent as thin layers alternating (for example upward and downward) through their chamber series and transfer heat to one another at both chamber walls. The corrugated plate profiles increase the turbulence and improve the heat transfer coefficients. Plate heat exchangers suitable for the inventive purpose are, for example, described in EP-A 107 9194, U.S. Pat. No. 6,382, 313, EP-A 123 2004 and WO 01/32301. Tube bundle heat exchangers are, for example, described in EP-A 700 893, EP-A 700 714 and DE-A 443 1949. Descriptions of spiral and ribbed tube heat exchangers can be found, for example, in Vauck/Müller, Grundoperationen chemischer Verfahrenstechnik [Basic Operations in Chemical Process Technology], 4th edition, Verlag Theodor Steinkopf, Dresden (1974) and in Ullmanns Encyclopädie der technischen Chemie, volume 2, Verfahrenstechnik I (Grundoperationen) [Process Technology I (basic operations)], 4th edition, 1972, p. 432 ff.

It is essential for the process according to the invention that the at least one substream I is conveyed forcibly through the at least one secondary space of the indirect circulation heat exchanger UW, with the aid of the pump P. Preferably, in accordance with the invention, the process according to the invention is therefore performed using forced circulation tubular heat exchangers (forced circulation tube bundle heat transferers) as circulation heat exchangers UW.

The at least one substream I is preferably forcibly conveyed within the tubes thereof.

For example, the process according to the invention can be performed using a three-flow tube bundle heat transferer through whose tubes the at least one substream I is forcibly conveyed.

In other words, the tube interiors form the secondary spaces of the heat transferer. The outer tube diameter may be 38 mm, with a wall thickness of the tubes of 2 mm. At a length of the tubes of 4800 mm, the total number thereof is, appropriately in application terms, 234 (78 tubes for each flow direction). The tube pitch is simultaneously advantageously 48 mm (30° distribution). 9 deflecting disks (disk thickness: in each case 5 mm) mounted between the tube plates (in which the exchanger tubes are secured) divide the cylindrical space (primary space) surrounding the heat transferer tubes into 10 longitudinal sections (segments). All 9 deflecting disks are in principle circular. The circle diameter is 859 mm. On each of the circular deflecting disks, however, a half-moon-shaped circle segment is cut out, whose area is 35.8% of the total area, so as to form a corresponding passage for steam as the heat carrier, these passages being provided opposite one another in alternating succession (otherwise, the deflecting plates are secured with sealing at the vessel wall; where the heat transferer tubes meet the deflecting plates, there are corresponding bores in the deflecting plates). Appropriately in application terms, steam is conducted as a heat carrier through space surrounding the heat transferer tubes. The inlets of steam and the at least one substream I into the three-flow tube bundle heat transferer are, favorably in application terms, on the same side of the heat transferer.

Alternatively, for the process according to the invention, it is also possible to use a thirteen-flow tube bundle heat transferer through whose tubes the at least one substream I is forcibly conveyed (as described hereinafter later in this document, referred to as thirteen-flow tube bundle heat transferer D*). Advantageously, in accordance with the invention, the cylinder which surrounds the primary space is equipped with a compensator (compensator dimensions: diameter=2.075 m; height=670 mm; 3 bellows; installation site at half the height of the vertical primary space), which enables low-tension thermal expansion of the apparatus in the course of heating and cooling.

The outer tube diameter may again be 38 mm, with a wall thickness of the tubes of 2 mm. At a length of the tubes of 5000 mm, the total number thereof is, appropriately in application terms, 1066 (82 tubes each for one flow direction). The tube pitch is simultaneously advantageously 47 mm (60° distribution). 9 deflecting disks (disk thickness: in each case 10 mm) mounted between the tube plates (in which the exchanger tubes are secured) divides the cylindrical space (primary space) surrounding the heat transferer tubes into 9 longitudinal sections (segments). All 9 deflecting disks are circular in principle. The circle diameter is 1734 mm. On each of the circular deflecting disks, however, a half-moon-shaped circle segment is cut out, whose area is 15% of the total area, so as to form a corresponding passage for steam as the heat carrier, these passages being provided opposite one another in alternating succession (otherwise, the deflecting plates are secured with sealing at the vessel wall; where the heat transferer tubes meet the deflecting plates, there are corresponding bores in the deflecting plates). Appropriately in application terms, steam is conducted as a heat carrier through the space surrounding the heat transferer tubes. The inlets of steam and the at least one substream I into the thirteen-flow tube bundle heat transferer are, favorably in application terms, on the same side of the heat transferer.

The working pressure on the pressure side of the pump P (prior to entry of the at least one substream I into the at least one secondary space of the circulation heat exchanger UW) in the process according to the invention is frequently 4 to 6 bar.

Otherwise, the procedure may, for example, be as described in DE-B 12 79 015, EP-A 780 360, DE-A 197 01 737, DE-A 23 39 519, DE-A 29 01 783, DE-A 103 32 758, German Application 10 2008 001 435.4, DE-A 10 2006 062 258, DE-A 10 2007 004 960 and WO 2004/035514.

Frequently, in processes according to the invention, the forced circulation heat exchanger is also configured as a forced circulation flash heat transferer, preferably a forced circulation tube bundle flash heat transferer. In contrast to the case of a pure forced circulation heat transferer, the former is normally separated from the feed point II in the separating column K by a throttle apparatus (for example, in the simplest case, by a perforated plate (or other orifice plate); another useful alternative is a valve).

The above measure suppresses boiling of the at least one substream I pumped in circulation within the at least one secondary space of the heat transferer ((heat exchanger)—for example in the tubes of the tube bundle heat transferer). The at least one substream I pumped in circulation is instead superheated within the at least one secondary space with respect to the gas pressure GD existing in the bottom space of the separating column K, and the boiling process is thus shifted completely to the passage side of the throttle apparatus (i.e., the contents of the tubes of the tube bundle heat transferer are present in monophasic form; the tube bundle heat transferer functions merely as a superheater). The throttle apparatus separates the heat transferer (heat exchanger; e.g. tube bundle heat exchanger) and the feed point II on the pressure side and enables, through suitable selection of the performance of the inventive pump, the establishment of a throttle admission pressure above the gas pressure GD existing in the bottom space, and above the boiling pressure, corresponding to the temperature $T^{RS}$, of the mass flow $\dot{M}^*$ flowing out of the at least one secondary space of the heat transferer. The evaporative boiling does not take place until beyond the throttle in flow direction. The employment of forced circulation flash heat exchangers UW is preferred in the process according to the invention.

The difference between the throttle admission pressure and the gas pressure GD existing in the bottom space is typically 0.1 to 5 bar, frequently 0.2 to 4 bar and in many cases 1 to 3 bar.

The temperature of the mass flow $\dot{M}^*$ flowing out of the at least one secondary space of the forced circulation flash heat exchanger UW when it leaves the at least one secondary space (still upstream of the throttle) is generally at least 5° C. above $T^{SU}$.

A substream of at least one of the two streams $\dot{M}$, $\dot{M}^*$ in the process according to the invention is discharged as a residual stream and is sent to its disposal, for example, to an incineration. Based on the stream $\dot{M}$ the residual stream is generally ≦1% by weight.

Preferably in accordance with the invention, only a substream of the stream $\dot{M}$ is discharged for the purpose of its disposal, and before the substream I of the stream $\dot{M}$ which then remains enters the at least one secondary space of the circulation heat exchanger UW. Adding an organic solvent (e.g. methanol) keeps this substream to be disposed of in fluid form.

The difference between the mass flow of Michael adducts ($\dot{m}_{in}$) fed to the redissociation apparatus as a constituent of the liquid F and the mass flow of Michael adducts ($\dot{m}_{out}$) discharged as a constituent of the aforementioned residual stream in the process according to the invention is a measure of the efficiency of the redissociation process.

In general, $[(\dot{m}_{in}-\dot{m}_{out})/\dot{m}_{in}]\times 100\%$ (=efficiency Q of the redissociation process) in the process according to the invention is at least 20%, preferably at least 30% or at least 40%. In many cases, Q in the process according to the invention is at least 50%. In favorable cases (with large residence time) Q may be virtually 100%. In general Q in the process according to the invention is, however, ≦90%. If required, the mass flow $\dot{M}$ can be withdrawn (it can be sucked in by the pump P) from the bottom space of the separating column K through a vortex breaker.

The success of the inventive procedure is attributed to the fact that there is still a small degree of redissociation of Michael adducts present in the bottoms liquid in said bottoms liquid (on its way to the pump P). When the temperature of the bottoms liquid is above the boiling point of the lowest-boiling redissociation product, this forms (in spite of the hydrostatic pressure which increases in the downward direction in the bottoms liquid) very small gas bubbles whose buoyancy in the bottoms liquid, at least in some cases, is insufficient to escape from the sucking action of the pump P (without such a continued redissociation, the bottoms liquid sucked in by the pump P would be essentially free of gas bubbles (cf. for example DE-A 103 32 758, page 9, paragraph [0082])). Over a prolonged operating time of the process according to the invention, these gas bubbles collect, as a result of the centrifugal forces, in the center of a closed radial impeller of a radial centrifugal pump (in a closed radial impeller, small gas bubbles can be conveyed only with difficulty) and block the impeller to an increasing degree ("vortex formation"), which finally has the consequence that the suction performance of the pump declines below the minimum degree required. In contrast, the aforementioned small gas bubbles can apparently be conveyed comparatively effectively by a radical centrifugal pump with semiopen impeller.

Under the same process technology conditions (temperature, density and viscosity of the medium conveyed, same pump housing, same drive motor, same impeller radius and same conveying vane configuration), the conveying output of a radial centrifugal pump with semiopen impeller is lower than that for a radial centrifugal pump with closed impeller, but this can be compensated if required by an increase in the impeller diameter. In any case, the use of a radial centrifugal pump with semiopen impeller in the process according to the invention ensures significantly more reliable liquid conveying.

The gas stream which remains in the partial condensation of the gas stream G in the process according to the invention and is discharged may, just like any portion of the condensate formed which has not been used as reflux liquid, have further uses in the same manner as already described in the prior art (for example DE-A 103 32 758, WO 2004/035514, WO 2008/090190, WO 2008/077767, EP-A 780 360, DE-A 197 01 737 and EP-A 1 357 105).

It will be appreciated that dispersants (e.g. surfactants) and/or defoamers can be added to the bottoms liquid of the separating column K, as recommended, for example, in German application 10 2008 001 435.4. Their addition can also be undertaken at the top of the separating column K.

The present invention thus comprises especially the following embodiments:

1. A process for redissociating Michael adducts which are present in a liquid F with a proportion by weight, based on the weight of the liquid F, of $\leq 10\%$ by weight and have been formed in the preparation of acrylic acid or esters thereof in a redissociating apparatus which comprises at least one pump P, a separating column K which consists, from the bottom upward, of a bottom space, a separating space which adjoins the bottom space and comprises separating internals, and a top space which adjoins the separating space, and in which the pressure in the gas phase decreases from the bottom upward, and an indirect circulation heat exchanger UW which has at least one secondary space and at least one primary space separated from the at least one secondary space by a material dividing wall D, in which the liquid F is conducted continuously into the separating column K with the feed temperature $T^Z$ at a feed point I which is above the lowermost separating internal in the separating column K, and, at the lowest point in the bottom space of the separating column K, the pump P is used to continuously withdraw a mass flow $\dot{M}$ of the liquid which effluxes into the bottom space through the separating internals and comprises Michael adducts with a temperature $T^{SU}$ so as to establish, in the bottom space, as the bottoms liquid, a level S of the liquid effluxing into it which is less than half the distance A, measured from the lowest point in the separating column K to the underside of the lowermost separating internal in the separating column K, while a gas pressure GD exists in the remaining space of the bottom space above this liquid level, and at least one substream I of the mass flow $\dot{M}$ is conducted through the at least one secondary space of the indirect circulation heat exchanger UW while being heated, by indirect heat exchange with a fluid heat carrier conducted simultaneously through the at least one primary space of the circulation heat exchanger UW, to a redissociation temperature $T^{RS}$ above the temperature $T^{SU}$, and at least one substream II from the mass flow $\dot{M}^*$ conducted out of the at least one secondary space of the circulation heat exchanger UW with the temperature $T^{RS}$ is recycled into the bottom space of the separating column K at a feed point II which is below the lowermost separating internal of the separating column K and above the level S of the bottoms liquid, in such a way that the at least one substream II in the bottom space of the separating column K is not directed toward the bottoms liquid, and a substream at least of one of the two streams $\dot{M}$, $\dot{M}^*$ is discharged as a residual stream, with the proviso that the redissociation temperature $T^{RS}$ is such that, firstly, as it flows through the at least one secondary space of the circulation heat exchanger UW, at least a portion of the Michael adducts present in the at least one substream I is redissociated to form the corresponding redissociation products, and, secondly, the at least one substream II recycled into the separating column K boils at the gas pressure GD existing in the bottom space at the feed point II, and the gas phase which forms in the course of boiling and comprises at least a portion of the redissociation products, following the gas pressure which decreases in the separating column K toward the top space of the separating column K, flows as a gas stream G comprising redissociation products into the top space of the separating column K and the gas stream G is partly condensed by direct and/or indirect cooling still in the top space of the separating column K and/or conducted out of the top space of the separating column K, the condensate formed is recycled at least partly as reflux liquid into the separating column K and the gas stream which remains in the partial condensation is discharged, wherein the pump P is a radial centrifugal pump with a semiopen radial impeller.

2. The process according to embodiment 1, wherein the Michael adducts present in the liquid F have been formed in the preparation of an ester from acrylic acid and a $C_1$- to $C_{10}$-alcohol, and the liquid F has the following contents:

| | |
|---|---|
| 1 to 30% by weight | of acrylic ester, |
| 40 to 80% by weight | of Michael adducts and |
| at least 15% by weight | of free-radical polymer of acrylic acid and/or acrylic ester, and |
| 0.1 to 2% by weight | of polymerization inhibitor. |

3. The process according to embodiment 1, wherein the Michael adducts present in the liquid F have been formed in the preparation of acrylic acid and the liquid F has the following contents:

| | |
|---|---|
| 10 to 50% by weight | of Michael adducts, |
| at least 40% by weight | of free-radical acrylic acid polymer, |
| up to 25% by weight | of monomeric acrylic acid, |
| up to 2% by weight | of polymerization inhibitor, and |
| up to 15% by weight | of other compounds. |

4. The process according to embodiment 1, wherein the Michael adducts present in the liquid F have been formed in the preparation of acrylic acid and the liquid F has the following contents:

| | |
|---|---|
| 10 to 50% by weight | of Michael adducts, |
| 40 to 80% by weight | of free-radical acrylic acid polymer, |
| 5 to 20% by weight | of monomeric acrylic acid, |
| 0.1 to 2% by weight | of polymerization inhibitor, and |
| 1 to 15% by weight | of other compounds. |

5. The process according to embodiment 3 or 4, wherein 40 to 60% by weight of the Michael adducts present in the liquid F are Michael acrylic acid dimers and 15 to 30% by weight are Michael acrylic acid trimers.

6. The process according to any one of embodiments 1 to 5, wherein the separating column K comprises dual-flow trays.

7. The process according to any one of embodiments 1 to 6, wherein the circulation heat exchanger UW is operated as forced circulation flash heat exchanger with the proviso that a throttle apparatus is present between the feed point II and the exit of the mass flow Ṁ from the at least one secondary space of the forced circulation flash heat exchanger, and the working pressure upstream of the throttle apparatus is greater than the gas pressure GD in the bottom space in flow direction.

8. The process according to any one of embodiments 1 to 7, wherein the redissociation process is promoted by conducting a stripping gas into the separating column K above the level S of the bottoms liquid and below the lowermost separating internal of the separating column K.

9. The process according to any one of embodiments 1 to 8, wherein the working pressure at the top of the separating column K is >1 to 3 bar.

10. The process according to any one of embodiments 1 to 9, wherein the circulation heat exchanger UW is a tube bundle heat exchanger.

11. The process according to embodiment 8, wherein the at least one substream II and the stripping gas are conducted into the bottom space by means of a coaxial double tube consisting of an inner tube and of an outer tube enclosing the latter, the stripping gas being conducted within the inner tube and the at least one substream II in the outer tube, and the inner tube having been thermally insulated from the outer tube.

12. The process according to embodiment 11, wherein both the stripping gas and the at least one substream II flow out of the coaxial double tube onto a baffle device which deflects both streams upward into the separating column K.

13. The process according to any one of embodiments 1 to 12, wherein the dynamic viscosity of the bottoms liquid at the temperature $T^{SU}$ is 30 to 90.

14. The process according to any one of embodiments 1 to 13, wherein the efficiency Q of the redissociation process is at least 20%.

U.S. Provisional Patent Application No. 61/122,154, filed on Dec. 12, 2008 is incorporated in the present application by reference. With respect to the abovementioned teachings, numerous changes to and deviations from the present invention are possible. It may therefore be assumed that the invention may be implemented other than specifically described herein, within the scope of the appended claims.

EXAMPLE AND COMPARATIVE EXAMPLE

The elements of the redissociation apparatus used were:
A) The pump P used was the KSB CPKN-C1.V 200-400 radial centrifugal pump from KSB Aktiengesellschaft in DE-67227 Frankenthal (Pfalz), with a double-action slip ring seal and an ethylene glycol (40% by weight)/water (60% by weight) mixture as the barrier fluid.
    In the comparative example, the aforementioned radial centrifugal pump was used as purchased from KSB, i.e. with a closed radial impeller.
    The same pump was used in the example, except that the top plate of the radial impeller had been removed (milled off) from the impeller vanes beforehand.
B) The indirect circulation heat exchanger UW used was the thirteen-flow tube bundle heat transferer (or heat exchanger) D* described in detail in the description of this document (manufacturing material: DIN type 1.4571 stainless steel on the tube side and 1.0425 on the outside).
C) The separating column K and the connecting elements were configured as follows:
    The manufacturing material of the separating column K was DIN type 1.4571 stainless steel. Just like all inlets and outlets, it was thermally insulated from the environment. As separating internals, it comprised 50 dual-flow trays (trickle sieve trays). The internal diameter of the separating column K was a uniform 2.4 m over all dual-flow trays. The dual-flow trays were arranged equidistantly in the stripping column, with a clear separation of 400 mm. Their orifice ratio was a uniform 12%. The hole diameter of the dual-flow trays was a uniform 14 mm (hole arrangement according to strict triangular pitch; distance of hole center to hole center=26 mm (trays 1 to 4 from the bottom), 25.5 mm (trays 5 to 8 from the bottom), 25 mm (trays 9 to 49 from the bottom) and 25.5 mm (tray 50 from the bottom). The tray thickness was in each case 4 mm. The lowermost of the dual-flow trays was mounted 7435 mm above the lower end of the column (i.e. A was 7435 mm measured from the lowest point in the column). Above the last dual-flow tray was mounted a chimney tray as a collecting tray. The upper edge of the chimney of this collecting tray was 29 525 mm above the lower end of the column. The chimneys were roofed and had an internal diameter of 316.7 mm and a height (calculated to the overflow height without the hat) of 1030 mm. The total number thereof was 12 and they were distributed homogeneously over the chimney tray. The collecting tray was configured in a single-wall design with a 2° gradient in the outward direction and with a side draw and draw stub (DN 200). The free gas cross section was approx. 30%. 4940 mm above the upper edge of the chimney (calculated without the hat), six tubes, whose internal diameter was 82 mm and whose wall thickness was 2.6 mm, were introduced through the column wall radially into the top space of the separating column K (the chimney tray formed the connection between top space and separating space of the separating column K). The introduction sites of the tubes were distributed equidistantly over the circumference of the column (angle enclosed by two adjacent tubes=60°).
    At a distance of 500 mm from the inner wall of the column, five of the six tubes were curved downward and ended in a circular nozzle orifice with an internal diameter of 2.5 inches.
    The sixth tube had a length of 800 mm extending from the inner wall of the column radially into the interior of the column. At a distance of 500 mm from the column wall, it had a circular nozzle orifice pointing downward with an internal diameter of likewise 2.5 inches. At the end of the length, this tube had an additional circular nozzle orifice with an internal diameter of 1¼ inches. The central jet of the corresponding spray cone had a vector component directed upward and formed an angle of 15° with the vertical to the column cross section.

Via a ring line which was mounted outside the column and to which the six tubes were attached, the six tubes were supplied with the liquid (condensate formed beforehand) for direct cooling of the gas stream G flowing through the chimney tray into the top space of the separating column K, and this liquid was sprayed into the column interior. The length of the separating column K (measured from the lowest point in the bottom space to the highest point in the top space) was 35 260 mm.

At the highest point in the top space was disposed the DN 500 outlet (internal diameter=498 mm) for the gas stream which remains in the direct cooling of the gas stream G.

At the lowest point in the bottom space was disposed the DN 400 outlet (internal diameter=398.4 mm) for the mass flow $\dot{M}$. It was equipped with a vortex breaker.

The connection of radial centrifugal pump and thirteen-flow tube bundle heat transferer was, in the following sequence toward the heat transferer, successively 1 DN 200 bend (90°, radius: 305 mm);
1 DN 200 cone to DN 300 (length: 203 mm);
1 straight DN 300 tube (length: 600 mm);
1 DN 300 bend (90°, radius: 457 mm);
1 straight DN 300 tube (length: 900 mm);
1 DN 300 bend (90°; radius: 457 mm);
1 straight DN 300 tube (length: 2800 mm);
1 DN 300 to DN 250 reduction (length: 203 mm);
2 DN 250 bends (90°, radius: 381 mm);
1 straight DN 250 tube (length: 900 mm);
1 DN 250 bend (90°, radius: 381 mm);
1 straight DN 250 tube (length: 6000 mm);
1 DN 250 bend (90°, radius: 381 mm);
1 straight DN 250 tube (length: 800 mm);
1 DN 250 to DN 300 reduction (length: 203 mm); and
1 DN 300 bend (90°, radius: 457 mm).

The connection from the outlet of the separating column K for the mass flow $\dot{M}$ to the thirteen-flow tube bundle heat transferer was, in the sequence which follows, toward the heat transferer, successively 1 DN 400 pipeline compensator (length approx. 510 mm);
1 straight DN 400 tube (length: approx. 2400 mm);
1 DN 400 bend (approx. 15°, radius: 610 mm);
1 DN 400 bend (90°, radius: 600 mm);
1 straight DN 400 tube (length: approx. 5000 mm); and
1 DN 400 to DN 250 reduction (length: 350 mm).

Between the exit of the mass flow $\dot{M}$* from the thirteen-flow tube bundle heat transferer and the bottom space of the separating column K a perforated plate was mounted as a throttle apparatus.

The reentry of the superheated "substream" II into the bottom space of the separating column K was configured as a coaxial double tube (tubes thermally insulated from one another) drawn into the middle of the bottom space cross section, where, curved in the downward direction, it pointed toward the level of the bottoms liquid. In flow direction beyond the end of the tube was mounted, secured on the outer tube shell, a baffle device which deflected the exit stream hitting it in the upward direction. In the outer ring of the coaxial double tube was conducted the superheated bottoms liquid; in the core of the coaxial double tube, the stripping gas ("support gas") was simultaneously metered in.

For the reflux liquid, 770 mm above the uppermost dual-flow tray and below the chimney tray, there was a distributor tube configured to form a closed circle (centered in the column and mounted horizontally, i.e. parallel to the column cross section) to which the reflux liquid was supplied. The inner diameter of the circle was 1870 mm. The outer diameter of the tube was 33.7 mm and the inner diameter of the tube was 25 mm. The circular distributor tube had 21 hole orifices whose internal diameter was 5 mm. Every second orifice of these was directed toward the underside of the chimney tray in order to keep it moist with reflux liquid. The central jet from the other half of the orifices pointed at an angle of 45° (to the horizontal on the column cross section), half of them downward into the middle of the column and half of them downward toward the column wall.

Additionally mounted in the periphery of the circular distributor tube were three precision jet tubes (length=200 mm, external diameter=6 mm, internal diameter=4 mm) which were distributed homogeneously over the circumference (angle formed 120°) and pointed radially outward. The exit from the precision jet tubes was directed toward ball valves through which it was possible to supply wash liquid to the column. Reflux liquid was fed to the separating part via the hole orifices and the jet tubes.

Between the eighth and ninth dual-flow trays (calculated from the bottom upward), there was a feed stub through which the liquid F to be subjected to the dissociation process was conducted into the separating column K. The feed was configured as an inserted tube which was conducted into the feed stub and had, on its underside, bores through which the liquid F was introduced homogeneously onto the tray below.

In the redissociation apparatus, the redissociation for the illustrative embodiment was operated in the steady state as follows:

The product gas mixture of a two-stage heterogeneously catalyzed partial gas phase oxidation of propylene (chemical grade) to acrylic acid, which was performed as described in the illustrative embodiment of WO 2008/090190, was subjected as in the illustrative embodiment of WO 2008/090190 to a fractional condensation in order to remove the acrylic acid present in the product gas mixture of the partial oxidation therefrom.

From the bottom region of the condensation column, as described in WO 2008/090190, high boiler liquid was withdrawn, which had the following contents:

| | |
|---|---|
| monomeric acrylic acid | 67.88% by wt., |
| Michael diacrylic acid (2AA) | 19.72% by wt., |
| Michael triacrylic acid (3AA) | 1.96% by wt., |
| Michael 4AA | 0.34% by wt., |
| Michael 5AA | 0.77% by wt., |
| Michael 6AA | 0.01% by wt., |
| Michael 7AA | 0.01% by wt., |
| Michael 8AA | 0.03% by wt., |
| Michael 9AA | 0.01% by wt., |
| Michael 10AA | 0.01% by wt., |
| free-radical acrylic acid polymer | 8.55% by wt., |
| fumaric acid | 0.27% by wt., |
| maleic acid | 0.27% by wt., |
| phthalic acid | 0.11% by wt., and |
| MEHQ + PTZ | 0.06% by wt.. |

3028 kg/h of this high boiler liquid were fed with a temperature of 102° C. to the separating column K of the redissociation apparatus (to the 8th tray from the bottom).

From the bottom space of the separating column K, the pump P sucked in a mass flow $\dot{M}$ with a temperature $T^{SU}$ of 169° C. (its dynamic viscosity was 60 mPas). The level S of the bottoms liquid settled at 82 cm.

The mass flow Ṁ had the following contents:

| | |
|---|---|
| monomeric acrylic acid | 9.3% by wt., |
| Michael diacrylic acid (2AA) | 10.62% by wt., |
| Michael triacrylic acid (3AA) | 5.19% by wt., |
| Michael 4AA | 2.69% by wt., |
| Michael 5AA | 3.38% by wt., |
| Michael 6AA | 0.1% by wt., |
| Michael 7AA | 0.1% by wt., |
| Michael 8AA | 0.2% by wt., |
| Michael 9AA | 0.1% by wt., |
| Michael 10AA | 0.1% by wt., |
| free-radical polymer | 63.14% by wt., |
| fumaric acid | 2% by wt. |
| maleic acid | 1.96% by wt., |
| phthalic acid | 0.78% by wt., and |
| MEHQ, PTZ and conversion products as the remainder up to 100% by weight. | |

A substream of 410 kg/h of the mass flow Ṁ was discharged as a residual stream.

The remaining substream of the mass flow Ṁ was pumped with the pump P as substream I (225 m³/h) through the tubes of the indirect circulation heat exchanger UW. At the same time, on the secondary space side of the circulation heat exchanger, 1700 kg/h of steam (19 bar absolute, 210° C.) were supplied as the heat carrier.

The inlet of the steam and the inlet of substream I into the thirteen-flow tube bundle heat transferer were, favorably in terms of application, on the same side of the heat transferer. The working pressure in flow direction upstream of the throttle apparatus (upstream of the orifice plate) was 3 bar, while the gas pressure GD in the bottom space was 1.7 bar. The temperature of the mass flow recycled from the primary space side of the circulation heat exchanger into the gas space of the bottom space was, in flow direction beyond the throttle apparatus, just before it exited from the coaxial double tube, 171° C.

At the top of the separating column K, a gas stream of 21 055 kg/h with a temperature of 67° C. and a pressure of 1.6 bar absolute was discharged. The amount of stripping gas supplied (1.7 bar, 148° C.) was 18 437 kg/h. This was residual gas withdrawn from the top of the condensation column, which had been compressed (together with cycle gas) with the aid of a multistage radial compressor to its working pressure and consisted to an extent of approx. 88% by weight of molecular nitrogen, to an extent of approx. 3% by weight of water, to an extent of approx. 5% by weight of molecular nitrogen and to an extent of approx. 2% by weight of carbon oxide. The reflux liquid had a temperature of 67° C. and was fed at a flow rate of 6500 kg/h to the uppermost dual-flow tray. It consisted essentially of acrylic acid condensed out of the gas stream G (approx. 90% by weight) and of water (approx. 6% by weight). The residual flow rate of the condensate stream which had been removed from the collecting tray and was not used as reflux liquid, for reasons of polymerization inhibition in a mixture with a small stream of bottoms liquid which comprised PTZ and MEQ and was withdrawn from the bottom of the condensation column, was conducted through a spiral heat exchanger cooled (in countercurrent) with water (inlet temperature=20° C.), which cooled it to 32° C. For the purpose of direct cooling of the acrylic acid-laden gas stream G which ascends through the chimney tray into the top space of the column, the total amount of the liquid mixture stream thus cooled indirectly was sprayed through the double ring distributor described into the top space of the separating column K.

FIG. 8 shows, over a section of 7 operating days, (abscissa; point of intersection with the ordinate=start of the 7-day period; right-hand end of the abscissa=end of the 7-day period) the profile of the flow rate circulated by the radial centrifugal pump with a semiopen impeller used (ordinate; essentially constant at 225 m³/h). The efficiency Q of the redissociation process was $[(\dot{m}_{in}-\dot{m}_{out})/\dot{m}_{in}]\times100\%=[(692.8\ \text{kg/h}-92.2\ \text{kg/h})/692.8\ \text{kg/h}]\times100\%=86.70\%$.

For the comparative example, the redissociation was conducted as follows:

same procedure in the same redissociation apparatus, but with the difference that the same radial centrifugal pump but with a closed impeller was used (same setting of the drive motor).

FIG. 9 shows, for the same case, again over a section of 7 operating days, the profile of the flow rate circulated by the radial centrifugal pump with a closed impeller (the start point on the ordinate is at approx. 240 m³ (STP)h).

The ordinates of FIGS. 8 and 9 have identical scales.

The irregular occurrence of performance declines is clearly visible.

The invention claimed is:

1. A process for redissociating Michael adducts which have been formed in the preparation of acrylic acid or esters thereof, comprising:

feeding a liquid F having a temperature $T^Z$ to a separating column K at a Feed Point I in a separating space of the column above a lowest separating internal;

separating the liquid F into at least a gas stream G comprising at least one of acrylic acid and an ester thereof as Michael addition redissociation products and a reflux liquid;

removing the gas stream G from a top space of the column K;

collecting the reflux liquid having a temperature $T^{SU}$ in a bottom space of the column K having a gas pressure GD to form a bottom liquid having a liquid level S;

removing a stream Ṁ from the bottom space of the column K;

pumping the stream Ṁ at $T^{SU}$ via a radial centrifugal pump P having a semiopen radial impeller through a secondary space of an indirect heat exchanger UW;

heating the stream Ṁ in the heat exchanger UW to form a stream Ṁ* having a temperature $T^{RS}$;

feeding the stream Ṁ* to a Feed Point II in the bottom space of the column K;

wherein a proportion of Michael addition product in the liquid F, is at least 10% by weight based on the weight of the liquid F, a pressure of the gas phase in the column K decreases from the bottom upward, the temperature $T^{RS}$ is greater than $T^{SU}$ and is such that at least a portion of the Michael adducts present in stream Ṁ* is redissociated to form the at least one of acrylic acid and an ester thereof as Michael addition redissociation products;

the Feed Point II is located below the lowermost separating internal of the separating column K and above the level S of the bottoms liquid, the level S is less than half a distance A measured from a lowest point of the column K to an underside of the lowermost separating internal, stream Ṁ* is fed at Feed Point II in such a way that the feed stream is not directed toward the bottoms liquid; and
the stream Ṁ* boils at the gas pressure GD.

2. The process according to claim 1, wherein a substream of at least of one of the two streams Ṁ, Ṁ* is discharged to waste as a residual stream.

3. The process according to claim 1, further comprising:
partially condensing the gas stream G by direct cooling, indirect cooling or a combination of direct and indirect cooling to form a condensate and a gas;
recycling the condensate at least partly as reflux liquid into the separating column K, and
discharging the gas stream.

4. The process according to claim 1, wherein the liquid F comprises:
1 to 30% by weight of acrylic ester,
40 to 80% by weight of Michael adducts and
at least 15% by weight of free-radical polymer of acrylic acid, an acrylic ester, or a combination thereof, and
0.1 to 2% by weight of a polymerization inhibitor, and
wherein the Michael adducts present in the liquid F have been formed in the preparation of an ester from acrylic acid and a $C_1$- to $C_{10}$-alcohol.

5. The process according to claim 1, wherein the liquid F comprises:
10 to 50% by weight of Michael adducts;
at least 40% by weight of free-radical acrylic acid polymer;
up to 25% by weight of monomeric acrylic acid;
up to 2% by weight of polymerization inhibitor; and
up to 15% by weight of other compounds, and
wherein the Michael adducts present in the liquid F have been formed in the preparation of acrylic acid.

6. The process according to claim 1, wherein the liquid F comprises:
10 to 50% by weight of Michael adducts,
40 to 80% by weight of free-radical acrylic acid polymer,
5 to 20% by weight of monomeric acrylic acid,
0.1 to 2% by weight of polymerization inhibitor, and
1 to 15% by weight of other compounds, and
wherein the Michael adducts present in the liquid F have been formed in the preparation of acrylic acid.

7. The process according to claim 1, wherein 40 to 60% by weight of the Michael adducts present in the liquid F are Michael acrylic acid dimers and 15 to 30% by weight are Michael acrylic acid trimers.

8. The process according to claim 1, further comprising: providing a stripping gas into the separating column K above the level S of the bottoms liquid and below the lowermost separating internal of the separating column K.

9. The process according to claim 1, wherein a working pressure at the top of the separating column K is from greater than 1 to 3 bar.

10. The process according to claim 8, wherein
the stream Ṁ* and the stripping gas are conducted into the bottom space of the column through a coaxial double tube consisting of an inner tube and of an outer tube enclosing the inner tube,
the stripping gas is conducted within the inner tube and the stream Ṁ* in the outer tube, and
the inner tube is thermally insulated from the outer tube.

11. The process according to claim 10, wherein the stripping gas and the stream Ṁ* flow out of the coaxial double tube onto a baffle device which deflects both streams upward into the separating column K.

12. The process according to claim 1, wherein a dynamic viscosity of the bottoms liquid at the temperature $T^{SU}$ is from 30 to 90.

13. The process according to claim 2, wherein
an efficiency Q of the redissociation process is at least 20%, wherein the efficiency Q is determined by the equation:

$$[(\dot{m}_{in} - \dot{M}_{out})/\dot{m}_{in}] \times 100\%$$

and ($\dot{m}_{in}$) is a mass flow of Michael adducts fed to the redissociation apparatus as a constituent of the liquid F and ($\dot{m}_{out}$) is a mass flow of Michael adducts discharged as a constituent of the residual stream.

14. The process according to claim 1, further comprising: adding a dissociation catalyst to the liquid F.

15. The process according to claim 14, wherein the dissociation catalyst added to the liquid F, is selected from the group consisting of mineral acids and organic acids other than acrylic acid.

* * * * *